United States Patent [19]

Kawai et al.

[11] Patent Number: 4,888,418
[45] Date of Patent: Dec. 19, 1989

[54] DERIVATIVES OF 13-DEOXYCARMINOMYCIN

[75] Inventors: Hiroyuki Kawai; Shohachi Nakajima, both of Maebashi; Tomio Takeuchi, Tokyo, all of Japan

[73] Assignee: Kirin Beer Kabushiki Kaisha, Tokyo, Japan

[21] Appl. No.: 166,707

[22] Filed: Mar. 11, 1988

[30] Foreign Application Priority Data

Mar. 14, 1987 [JP] Japan .................................. 62-59286

[51] Int. Cl.$^4$ ........................................... C07H 15/24
[52] U.S. Cl. .................................................. 536/6.4
[58] Field of Search ........................................ 536/6.4

[56] References Cited

U.S. PATENT DOCUMENTS 4,585,859 4/1986 Mosher et al. ....................... 536/6.4
4,710,564 12/1987 Otake et al. .......................... 536/6.4

FOREIGN PATENT DOCUMENTS 0188293 7/1986
2036021 6/1980 United Kingdom .
2048245 12/1980 United Kingdom .

OTHER PUBLICATIONS

Morrison and Boyd, *Organic Chemistry*, 5th Edition, 1983.
Albert Lehninger, Biochemistry: The Molecular Basis of Cell Structure & Funtion, Worth Publishers: New York, 1970.
Takahashi et al., "The Structure of Baumycins A1, A2, B1, B2, C1, and C2," The Journal of Antibiotics, vol. 30, Jul. 1977, pp. 622-624.
Chemical Abstracts, vol. 107, No. 17, Oct. 26, 1987, p. 578, Abst. No. 152859c, Kawai et al., "Manufacture of Anticoncer13 -Deoxocarminomycin and its N-(2",3-"-Alkylioenedioxy)propylderivatives", Columbus, Ohio, U.S.
Chemical Abstracts, vol. 107, No. 19, Nov. 9, 1987, p. 582, Abst. No. 174374t; Otake et al., "Anthracycline Compounds and Antitumor Agents Containing them," Columbus, Ohio, U.S.
Chemical Abstracts, vol. 101, No. 1, Jul. 2, 1984, p. 483,. Abstract No. 5554x, Wolfgang, I. et al., "Antaracydine Antibiotic and its Aghycane".
Acton, E. M. et al., "Approaches to More Effective Anthracyclines by Analog Synthesis and Evaluation," in: Anthracycline Antibiotics, Paper Symposium 1982, pp. 119-139, Academic Press.
Morrison and Boyd, *Organic Chemistry* (Boston, Allyn and Bacon, 1983) pp. 27-28, 15-19.
Lehninger, Albert, Biochemistry: The Molecular Basis of Cell Structure and Function, (Worth Publishers, New York, 1970), p. 89.
Chem. Abstracts, vol. 101, p. 483.

Anthracycline Antibiotics, Paper Symposium 1982, pp. 119-139, Academic Press
"Approaches to More Effective Anthracyclines by Analog Synthesis . . ." p. 124, Emacton.

*Primary Examiner*—Joseph L. Schofer
*Assistant Examiner*—Gary L. Kunz
*Attorney, Agent, or Firm*—Ladas & Parry

[57] ABSTRACT

An anthracycline compound (13-deoxycarminomycin) selected from the group consisting of anthracycline compounds represented by the following formula

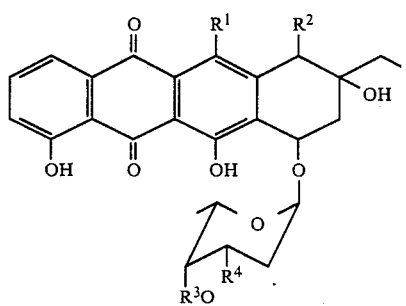

$R_1$ is a hydroxy group,
$R_2$ represents a hydrogen atom or a hydroxyl group,
$R_3$ is a hydrogen atom,
$R_4$ represents one of the following groups (a) to (d)

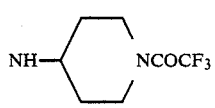

(a)

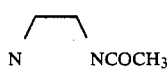

(b)

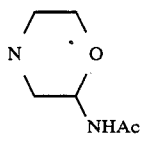

(c)

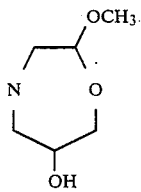

(d)

and if $R_2$ is hydroxyl, $R_4$ is not (d).

2 Claims, No Drawings

DERIVATIVES OF 13-DEOXYCARMINOMYCIN

BACKGROUND OF THE INVENTION

The present invention relates to novel anthracycline compounds and further to the use of the novel anthracycline compounds, that is, the use thereof as antitumor agents.

Daunomycin (U.S. Pat. No. 3,616,242) and adriamycin (U.S. Pat. No. 3,590,028) are known as anthracycline type compounds. These compounds are extensively used in clinical stages. However, they are known to have serious side effects such as cardiotoxicity, impairment of bone marrow and the like, and thus their uses remain only unsatisfactory.

On the other hand, preparation of novel and miscellaneous analogous compounds by methods including fermentation, semi-synthesis, microbial transformation and the like have been attempted, and there have already been reported several compounds such as 4'-epiadriamycin (Japan Science Society Press, Tokyo/University Park Press, Baltimore, 292–312, 1978), 4-demethoxyadriamycin (Cancer Treat. Rep., 60: 829, 1976), and THP-adriamycin (J. Antibiotics 32: 1082, 1979).

For the purpose of providing a useful anthracycline derivative, we have also proposed morpholino derivatives of 13-deoxocarminomycin, 13-deoxo-10-hydroxycarminomycin and 13-deoxo-11-deoxycarminomycin (referred to hereinafter as R20 substances) represented by the formula (I) (Japanese Patent Application Laid-Open Nos. 167696/86 and 16495/87):

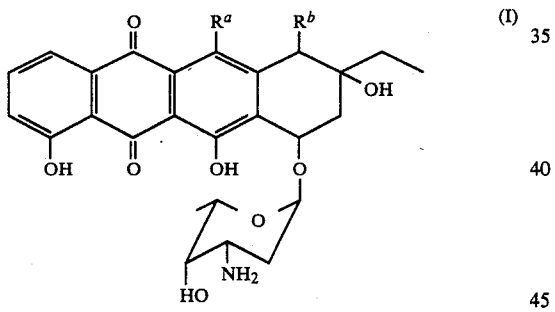

(1) 13-deoxocarminomycin (referred to hereinafter as R20X), $R^a$: OH, $R^b$: H,
(2) 13-deoxo-10-hydroxycarminomycin (referred to hereinafter as R20X2), $R^a$: OH, $R^b$: OH, and
(3) 13-deoxo-11-deoxycarminomycin (referred to hereinafter as R20Y5), $R^a$: H, $R^b$: H.

SUMMARY OF THE INVENTION

The present invention relates to novel compounds corresponding to the derivatives of R20 substances represented by the above formula (I).

In other words, the anthracycline compounds according to the present invention are selected from the group consisting of an anthracycline compound represented by the following general formula [A] or an acid addition salt thereof and an anthracycline compound represented by the following general formula [B] or an acid addition salt thereof.

The present invention also relates to the use of the novel compounds.

The antitumor agents according to the present invention contain as an active ingredient the anthracycline compound represented by the following general formulae [A] or [B] or an acid addition salt thereof:

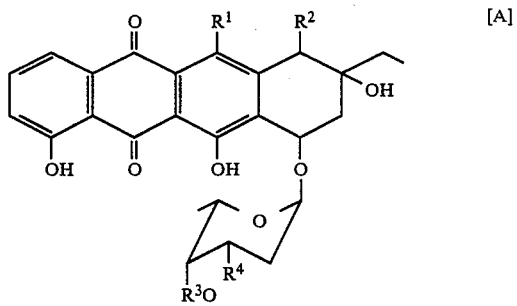

wherein $R^1$ to $R^4$ have the following meanings:
(i) $R^1$ and $R^2$ represent a hydrogen atom or a hydroxyl group;
(ii) $R^3$ represents a hydrogen atom or a group

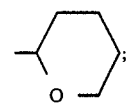

(iii) if $R^3$ is a hydrogen atom, $R^4$ represents either one of the following groups:

wherein $R^5$ represents a hydrogen atom; an alkyl group, preferably one having 1 to 10 carbon atoms; an alkenyl group, preferably one having 2 to 10 carbon atoms; an alkynyl group, preferably one having 2 to 10 carbon atoms; a fluoroalkyl group, preferably one having 1 to 10 carbon atoms; an aryl group, preferably a phenyl group, a lower alkyl substituted phenyl group or a naphthyl group; an aralkyl group, preferably one having an aryl moiety and an alkyl moiety as defined above; or a group $-O-(CH_2)_n-X-(CH_2)_nCOOH$, wherein X represents a hetero atom such as oxygen or sulfur, and n denotes an integer of 1 to 20;

wherein $R^6$ and $R^7$ respectively represent a hydrogen atom, and alkyl group, an alkenyl group, an alkynyl group, and aryl group, an aralkyl group or an alkyl group which may have a hydroxyl group, a carboxyl group, an amino group or an ether, sulfide or amide bonding, provided that $R^6$ and $R^7$ will not represent a hydrogen atom at the same time, and these groups are preferably as defined for $R^5$;

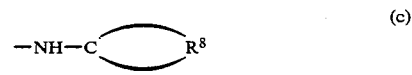

wherein $R^8$ represents an alkylene group which may have a hydroxyl group, a carboxyl group or an amino group or an ether, sulfide or amide bonding, preferably having the total carbon atoms up to 6;

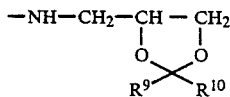 (d)

wherein $R^9$ and $R^{10}$ respectively represent an alkyl group, provided that $R^9$ and $R^{10}$ will not represent a methyl group at the same time, and preferably these groups are as defined for $R^5$;

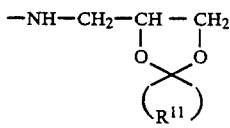 (e)

wherein $R^{11}$ represents an alkylene group, preferably having the total carbon atoms up to 6, except that $R^{11}$ is $-(CH_2)_5-$;

$-NH-CH_2R^{12}$ (f)

wherein $R^{12}$ represents the part except the aldehyde group of a 16 membered macrolide having the aldehyde group at the side chain at the 6-position of an aglycone,

 (g)

wherein $R^{13}$ represents an alkylene group which may include a hydroxyl group, a carboxyl group, an amino group or an ether, sulfide or amide bonding, preferably having the total carbon atoms up to 6, provided that $R^4$ will not represent a group

(h)

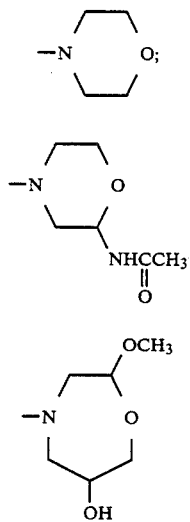

(iv) if $R^3$ is a group

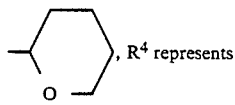, $R^4$ represents a group $-NH_2$ or 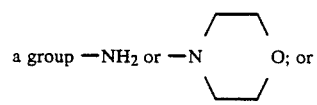; or

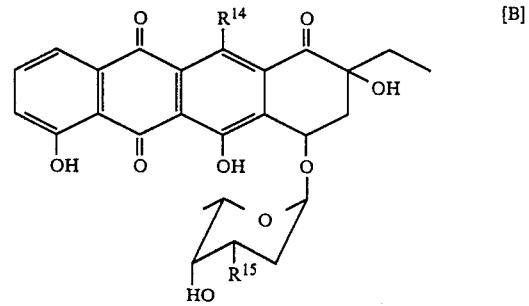 [B]

wherein $R^{14}$ represents a hydrogen atom or a hydroxyl group, and $R^{15}$ represents a group $-NH_2$ or 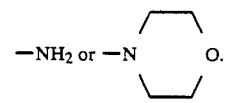.

DETAILED DESCRIPTION OF THE INVENTION

Production of the compounds of the present invention

Preparation of the parent compound

The compounds of the present invention are produced from the R20 substances as primary raw materials. The R20 substances are well-known substances, and the method of preparation and the physicochemical properties thereof are as described in Japanese Patent Application Laid-Open Nos. 167696/86 and 16495/87. Further, the microorganism to be used for the preparation of the R20 substances has been deposited with Fermentation Research Institute, of the Agency of Industrial Sciences and Technology, Japan with "FRI No. 945".

Production of the compounds of the present invention

The process for producing derivatives of the R20 substances as the leading compounds is described below.

Among the compounds of the present invention, the compound described in the paragraph (iii)-(a) may be produced by reacting an acid chloride or an acid anhydride with the compound represented by the formula (I) in a basic solvent such as pyridine or heating the compound represented by the formula (II) together with the compound represented by the formula (I) in a solvent in which both of the compounds are soluble, for example, dioxane.

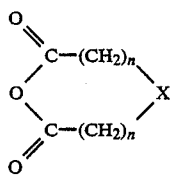

(II)

wherein X represents a hetero atom and n denotes 1 to 20.

The compounds described in the paragraphs (iii)-(b), (c), (d), (e) and (f) can be produced by reacting the R20 substance represented by the formula (I) with a compound having an aldehyde or ketone such as glyceraldehyde, acetol, or josamycin. The solvents used for the reaction include acetonitrile, methanol, ethanol, water, chloroform, dichloromethane, carbon tetrachloride or the like alone or as a mixture thereof, preferably a mixed solvent of chloroformmethanol. The reaction is generally conducted preferably in the presence of a reducing agent such as sodium borohydride or sodium cyanoborohydride. The reducing agent is used in an amount of at least 1 mole, preferably 1–3 moles to 1 mole of the R20 substance. The compound having an aldehyde or a ketone is conveniently used in an amount of 1.5 moles or more, preferably 5 moles or more to 1 mole of the R20 substance. The reaction temperature is generally within the range from freezing point of a solvent used to 50° C., preferably around room temperature.

Alternately, the compounds described in the paragraphs (iii)-(b), (c), (d), (e) and (f) can be produced by reacting the R20 substances with a compound having a removing group such as a haloalkane, a haloalkene, a haloalkyne, an araklyl halide or the like. The reaction is generally carried out in a solvent. The solvents which can be used include aprotic solvents such as N, N-dimethylformamide, tetrahydrofuran and the like. The reaction is ordinarily conducted in the presence of a base such as triethylamine or diisopropylethylamine. The base is used in an amount of at least 1.5 moles or more, preferably 2 to 5 moles per 1 mole of the R20 substance. A compound having a removing group is preferably used in an amount of 2 to 4 moles to 1 mole of the R20 substance. The reaction is preferably conducted at a temperature of 0° to 50° C., particularly around room temperature.

The compound described in the paragraphs (iii)-(g) and (h) can be produced by reacting the R20 substance with a compound having a dialdehyde at the terminal or a compound having a removing group such as halogen or the like at the terminal. The reaction is conducted under the same reaction conditions as those for producing the compounds described in the paragraphs (iii)-(b), (c), (d), (e) and (f).

The compound described in the paragraph (iv) can be produced by reacting 3,4-dihydro-2H-pyran with a compound represented by the formula (I) in an aprotic solvent such as tetrahydrofuran or N, N-dimethylformamide in the presence of an acid catalyst such as p-toluenesulfonic acid and reacting the 4′-tetrahydropyranylated product of the compound represented by the formula (I) with a compound having a dialdehyde at the terminal and a reducing agent such as sodium cyanoborohydride, respectively, in one equivalent amount and two equivalent amounts in an organic solvent or a mixture of an organic solvent and water such as methanol, acetonitrile, or a mixture of chloroform and methanol at room temperature.

The compound represented by the formula [B] can be obtained by dissolving the compound represented by the formula (I) in an organic solvent, preferably in acetone, adding thereto an oxidizing agent, preferably Jones reagent and stirring the mixture at room temperature for 0.5 to 4 hours.

The compounds represented by the formulae [A] and [B] can be isolated from the reaction mixture by a purification method well-known in the art of preparing gylcoside derivatives of anthracyclines. For example, the desired substance can be isolated in a pure form by extracting the reaction mixture with an organic solvent immiscible with water, preferably chloroform, methylene chloride or the like, concentrating the solvent layer, and subjecting the residue to a separation and purification procedure such as silica gel column chromatography or preparative thin-layer chromatography on a silica gel or by gel filtration chromatography on Sephadex LH20 or the like.

The group of the compounds represented by the formulae [A] and [B] can be converted to their acid addition salts according to a method well-known per se by treating with an inorganic acid such as hydrochloric acid, sulfuric acid, or phosphoric acid or an organic acid such as acetic acid, propionic acid, maleic acid, oleic acid, palmitic acid, citric acid, succinic acid, tartaric acid, fumaric acid, glutamic acid, pantothenic acid, or laurylsulfonic acid.

Specific Examples of the Compounds

Specific examples of the compounds obtained according to the present invention are as follows.
Chemical Name:
1. N-trifluoroacetyl-13-deoxocarminomycin,
2. N-carboxymethoxyacetyl-13-deoxocarminomycin,
3. N-ethyl-13-deoxocarminomycin,
4. N,N-diethyl-13-deoxocarminomycin,
5. N-benzyl-13-deoxocarminomycin,
6. N-allyl-13-deoxocarminomycin,
7. N,N-diallyl-13-deoxocarminomycin,
8. N-(2″-hydroxypropyl)-13-deoxocarminomycin,
9. N-[(2″S)-2″,3″-dihydroxypropyl]-13-deoxocarminomycin,
10. N-[(2″R)-2″,3″-dihydroxypropyl]-13-deoxocarminomycin,
11. N-(1″-hydroxy-2″-propyl)-13-deoxocarminomycin,
12. A, B N-(1″,1″-dimethoxy-2″-propyl)-13-deoxocarminomycin,
13. N-carboxymethyl-13-deoxocarminomycin,
14. N-cyclopentyl-13-deoxocarminomycin,
15. N-(4″-tetrahydropyranyl)-13-deoxocarminomycin,
16. N-(4″-piperidinyl)-13-deoxocarminomycin,
17. N-(1‴-trifluoroacetyl-4″-piperidinyl)-13-deoxocarminomycin,
18. N-(1‴-trifluoroacetyl-4″-piperidinyl)-13-deoxo-10-hydroxycarminomycin,
19. N-(2″,3″-diethylidenedioxypropyl)-13-deoxocarminomycin,
20. N-(2″,3″-dipropylidenedioxypropyl)-13-deoxocarminomycin,
21. N-(2″,3″-cyclopentylidenedioxypropyl)-13-deoxocarminomycin,
22. N-(2″,3″-cycloheptylidenedioxypropyl)-13-deoxocarminomycin,
23. 3′-deamino-3′-(1″-piperidino)-13-deoxocarminomycin, 24. 3'-deamino-3'-(1"'-acetyl-4"-piperazinyl)-13-deoxocarminomycin,
25. 3'-deamino-3'-(1"'-acetyl-4"-piperazinyl)-13-deoxo-10-hydroxycarminomycin,
26. 3'-deamino-3'-[(2"R)-2"-acetamido-4"-morpholino]-13-deoxocarminomycin,
27. 3'-deamino-3'-[(2"R)-2"-acetamido-4"-morpholino]-13-deoxo-10-hydroxycarminomycin,
28. A, B 3'-deamino-3'-(6"-hydroxy-2"-methoxy-4"-perhydroxazepinyl)-13-deoxocarminomycin,
29. A, B 4'-O-tetrahydropyranyl-13-deoxocarminomycin,
30. A, B 3'-deamino-3'-(4"-morpholino)-4'-O-tetrahydropyranyl-13-deoxocarminomycin,
31. N-[18"-(18"-deoxojosamycinyl)]-13-deoxocarminomycin,
32. 3'-deamino-3'-(4"-morpholino)-13-deoxo-10-oxocarminomycin, wherein A and B are stereoisomers.
Structure

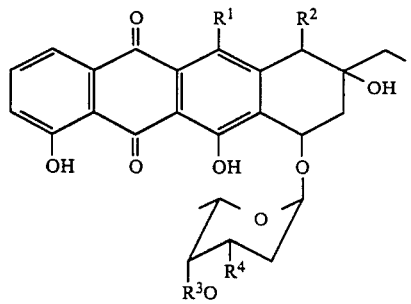

The compounds 1 to 31 have the following structures for $R^1$, $R^2$, $R^3$ and $R^4$ in the formula [A]:

| | $R^1$ | $R^2$ | $R^3$ | $R^4$ |
|---|---|---|---|---|
| 1 | OH | H | H | $NHCOCF_3$ |
| 2 | OH | H | H | $NHCOCH_2OCH_2COOH$ |
| 3 | OH | H | H | $NH(C_2H_5)$ |
| 4 | OH | H | H | $N(C_2H_5)_2$ |
| 5 | OH | H | H | $NHCH_2C_6H_5$ |
| 6 | OH | H | H | $NHCH_2CH=CH_2$ |
| 7 | OH | H | H | $N(CH_2CH=CH_2)_2$ |
| 8 | OH | H | H | $NHCH_2CH(OH)CH_3$ |
| 9 | OH | H | H | (S) $NHCH_2CH(OH)CH_2OH$ |
| 10 | OH | H | H | (R) $NHCH_2CH(OH)CH_2OH$ |
| 11 | OH | H | H | ![NH-CH(CH3)-CH2OH] |
| 12 | OH | H | H | ![NH-CH(CH3)-CH(OMe)2] |
| 13 | OH | H | H | $NHCH_2COOH$ |
| 14 | OH | H | H | ![NH-cyclopentyl] |
| 15 | OH | H | H | ![NH-tetrahydropyranyl] |
| 16 | OH | H | H | ![NH-piperidinyl-NH] |
| 17 | OH | H | H | ![NH-piperidinyl-NCOCF3] |
| 18 | OH | OH | H | ![NH-piperidinyl-NCOCF3] |

-continued

| | R¹ | R² | R³ | R⁴ |
|---|---|---|---|---|
| 19 | OH | H | H | NH-CH₂-CH(O-)(O-) spiro with diethyl ketal |
| 20 | OH | H | H | NH-CH₂-CH(O-)(O-) dipropyl ketal |
| 21 | OH | H | H | NH-CH₂-CH(O-)(O-) cyclopentyl spiroketal |
| 22 | OH | H | H | NH-CH₂-CH(O-)(O-) cycloheptyl spiroketal |
| 23 | OH | H | H | piperidin-1-yl |
| 24 | OH | H | H | 4-(acetyl)piperazin-1-yl (NCOCH₃) |
| 25 | OH | OH | H | 4-(acetyl)piperazin-1-yl (NCOCH₃) |
| 26 | OH | H | H | 3-(acetamido)morpholin-4-yl, NHAc (R) |
| 27 | OH | OH | H | 3-(acetamido)morpholin-4-yl, NHAc (R) |
| 28 | OH | H | H | 3-methoxy-5-hydroxymorpholin-4-yl (OCH₃, OH) |

-continued

| | R¹ | R² | R³ | R⁴ |
|---|---|---|---|---|
| 29 | OH | H | (tetrahydropyranyl-O-) | NH₂ |
| 30 | OH | H | (tetrahydropyranyl-O-) | (morpholino) |
| 31 | OH | H | H | (complex macrolide structure shown) |

The compound 32 has the following structure:

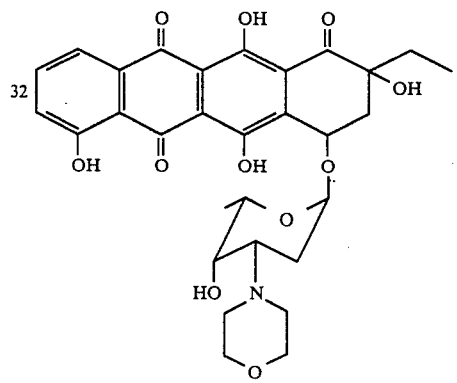

Use of the Derivatives

The derivatives of the present invention have carcinostatic activity and thus are useful as a medicament.

(1) Antitumor agent

The derivatives of the present invention exhibited antitumor activities with respect to leukemia of experimental animals as shown in Table 1.

The data shown in Table 1 are the survival rate(%) of $CDF_1$ mice, to which a suspension of P388 leukemia cells have been inoculated intraperitoneally in an amount of $1 \times 10^6$/mouse, and the derivative has been administered intraperitoneally (ip) or intravenously (iv) on day 1 and day 5 after inoculation, based on the survival days of the control group to which physiological saline has been administered.

TABLE 1

Antitumor activity of the derivatives

| Compound | Administration route | Dose (mg/kg) | survival rate (%) |
|---|---|---|---|
| 1 | ip | 2 | 142 |
| | | 4 | 112 |
| | | 8 | 82 |

TABLE 1-continued

Antitumor activity of the derivatives

| Compound | Administration route | Dose (mg/kg) | survival rate (%) |
|---|---|---|---|
| 2 | iv | 1 | 104 |
| | | 2 | 109 |
| | | 4 | 98 |
| | | 8 | 104 |
| | | 16 | 104 |
| | | 32 | 93 |
| 3 | iv | 2 | 95 |
| | | 4 | 108 |
| | | 8 | 148 |
| | | 16 | 139 |
| 4 | iv | 2 | 93 |
| | | 4 | 99 |
| | | 8 | 95 |
| | | 16 | 108 |
| 5 | iv | 2 | 103 |
| | | 4 | 112 |
| | | 8 | 155 |
| | | 16 | 190 |
| | | 32 | 73 |
| 6 | iv | 4 | 99 |
| | | 8 | 108 |
| | | 16 | 172 |
| | | 32 | 142 |
| 7 | iv | 4 | 95 |
| | | 8 | 129 |
| | | 16 | 155 |
| | | 32 | 134 |
| 8 | iv | 2 | 102 |
| | | 4 | 115 |
| | | 8 | 182 |
| | | 16 (bis) | 210 |
| 9 | iv | 1 | 91 |
| | | 2 | 94 |
| | | 4 | 94 |
| | | 8 | 91 |
| 10 | iv | 1 | 91 |
| | | 2 | 94 |
| | | 4 | 114 |
| | | 8 | 94 |
| 11 | iv | 2 | 98 |
| | | 4 | 114 |
| | | 8 | 98 |
| | | 16 | 108 |
| 12 A | iv | 2 | 91 |

TABLE 1-continued

Antitumor activity of the derivatives

| Compound | Administration route | Dose (mg/kg) | survival rate (%) |
|---|---|---|---|
|  |  | 4 | 108 |
|  |  | 8 | 108 |
|  |  | 16 | 155 |
| 12 B | iv | 2 | 101 |
|  |  | 4 | 114 |
|  |  | 8 | 104 |
|  |  | 16 | 118 |
| 13 | iv | 0.25 | 115 |
|  |  | 0.5 | 115 |
|  |  | 1.0 | 115 |
| 14 | iv | 1 | 104 |
|  |  | 2 | 98 |
|  |  | 4 | 98 |
|  |  | 8 | 104 |
| 15 | iv | 1 | 101 |
|  |  | 2 | 101 |
|  |  | 4 | 104 |
|  |  | 8 | 104 |
|  |  | 16 | 109 |
|  |  | (ter) |  |
| 16 | iv | 1 | 111 |
|  |  | 2 | 104 |
|  |  | 4 | 111 |
|  |  | 8 | 107 |
|  |  | 16 | 104 |
| 17 | iv | 1 | 93 |
|  |  | 2 | 120 |
|  |  | 4 | 180 |
|  |  | 8 | 210 |
| 18 | iv | 0.5 | 115 |
|  |  | 1 | 165 |
|  |  | 2 | 196 |
|  |  | 4 | 239 |
|  |  | 8 | 101 |
| 19 | ip | 4 | 138 |
|  |  | 8 | 148 |
|  |  | 16 | 236 |
|  |  | 32 | 127 |
| 20 | ip | 2 | 114 |
|  |  | 4 | 121 |
|  |  | 8 | 148 |
|  |  | 16 | 212 |
| 21 | ip | 4 | 138 |
|  |  | 8 | 156 |
|  |  | 16 | 211 |
|  |  | 32 | 120 |
| 22 | ip | 4 | 120 |
|  |  | 8 | 127 |
|  |  | 16 | 138 |
|  |  | 32 | 116 |
|  |  | (quarter) |  |
| 23 | iv | 1 | 104 |
|  |  | 2 | 116 |
|  |  | 4 | 112 |
|  |  | 8 | 149 |
|  |  | 16 | 202 |
| 24 | iv | 0.25 | 112 |
|  |  | 0.5 | 141 |
|  |  | 1 | 167 |
|  |  | 2 | 167 |
| 25 | iv | 0.125 | 106 |
|  |  | 0.25 | 137 |
|  |  | 0.5 | 146 |
|  |  | 1.0 | 190 |
|  |  | 2.0 | 186 |
|  |  | 4.0 | 72 |
| 26 | iv | 1 | 103 |
|  |  | 2 | 128 |
|  |  | 4 | 157 |
|  |  | 8 | 186 |
|  |  | 16 | 281 |
| 27 | iv | 0.5 | 101 |
|  |  | 1 | 139 |
|  |  | 2 | 138 |
|  |  | 4 | 161 |
|  |  | 8 | 173 |
|  |  | 16 | 142 |
| 28A | iv | 1 | 109 |
|  |  | 2 | 90 |
|  |  | 4 | 104 |
|  |  | 8 | 120 |
|  |  | 16 | 165 |
|  |  | 32 | 270 |
|  |  | (quinquies) |  |
| 28B | iv | 0.25 | 116 |
|  |  | 0.50 | 157 |
|  |  | 1 | 161 |
|  |  | 2 | 191 |
|  |  | 4 | 75 |
|  |  | 8 | 67 |
| 29A | iv | 2 | 134 |
|  |  | 4 | 181 |
|  |  | 8 | 95 |
| 29 B | iv | 2 | 168 |
|  |  | 4 | 146 |
|  |  | 8 | 173 |
|  |  | 16 | 125 |
| 30 A | iv | 2 | 125 |
|  |  | 4 | 147 |
|  |  | 8 | 164 |
|  |  | 16 | 168 |
|  |  | 32 | 39 |
| 30 B | iv | 2 | 108 |
|  |  | 4 | 138 |
|  |  | 8 | 168 |
|  |  | 16 | 164 |
|  |  | 32 | 34 |
| 31 | iv | 32 | 142 |
| 32 | iv | 2 | 103 |
|  |  | 4 | 103 |
|  |  | 8 | 110 |
|  |  | 16 | 103 |
|  |  | 32 | 103 |

(2) Antitumor agent

As shown above, the derivatives of the anthracycline compounds of the present invention have been confirmed to have antitumor activity relative to animal tumors, particularly malignant tumors.

Accordingly, the derivatives of the present invention can be used as an antitumor agent or a tumor therapeutic agent.

The derivatives of the present invention as the antitumor agent can be administered in an appropriate optional administration route or in a dosage form which will be determined by the adopted administeration route. The derivatives as a medicament has generally a form which has been diluted with a pharmaceutically acceptable carrier or diluent.

When the derivative of the present invention as the antitumor agent is practically administered, it may typically be injected as a solution in distilled water for injection or physiological saline. Specifically for veterinary application, the injectional methods of intraperitoneal injection, subcutaneous injection, intravascular injections such as intravenous or intraarterial injection and local application may be used, and for the application to human subjects injectional methods including intra-vascular injections such as intravenous or intra-arterial injection or local application may be used.

The dose of the derivatives of the present invention is determined to ensure that the total dose of continuous or intermittent dosage will not exceed a certain level in consideration of the results of animal tests and various situations. It is needless to say that the dose of the derivative specifically varies depending on application methods, situations of patients or subject animals such as age, body, weight, sex, sensitivity, feed, application time, drugs to be used together, patients or the conditions of the patients. Appropriate dose and administering times under a certain condition must be determined by an optimal dosage determining test by a specialist medical doctor based on the above instruction.

EXPERIMENTAL EXAMPLES

The present invention will be illustrated more fully and specifically by the following experimental examples. The present invention is not intended to be limited to these examples.

REFERENTIAL EXAMPLE

The percentage (%) means hereinafter "w/v %".

REFERENTIAL EXAMPLE 1 (PREPARATION OF THE R20 SUBSTANCE)

(1) Preparation of mother seed

The fermentation broth used is one in which the ingredients having the following contents have been dissolved in 1 liter of water and then adjusted to pH 7.2.

| Polypeptone | 1% |
| Molasses | 1% |
| Meat extract | 1% |

A 100 ml portion of the above fermentation broth was placed and sterilized in a 500-ml Erlenmeyer flask, and one platinum loopfull of *Actinomadura roseviolacea* R20 taken from a slant was inoculated into the flask and cultured in a rotary shaker (200 rpm) at 27° C. for 5 days to obtain a mother seed.

(2) Cultivation

The fermentation broth used was the one in which the ingredients having the following contents had been dissolved in 1 liter of water and adjusted to pH 7.4.

| Glucose | 2.5% |
| Soy bean powder | 1.5% |
| Dry yeast | 0.2% |
| (Precipitated) calcium carbonate | 0.4% |

Twenty-five liters of the above-mentioned fermentation broth was placed and sterilized in a 50-liter jar-fermenter. Three vials of the above-mentioned mother seeds were inoculated into the fermentation broth, and cultured with aeration (1 vvm) and agitation (200 rpm) at 27° C. for 7 days.

(3) Collection of R20X

After cultivation, the fermentation broth was filtered to separate the bacterial cells and the filtrate. The filtrate was adjusted to pH 2 with 1N HCl and adsorbed on a column (10×40 cm) of "Diaion HP20" (manufactured by Mitsubishi Chemical Industries Ltd.). After washing with distilled water and 60% methanol, elution was conducted with methanol. The eluate was concentrated. The concentrate was adjusted to pH 8.5 and extracted three times with a mixture of chloroform-methanol (9:1). The extract was concentrated, and hexane was added in an amount of 6 times that of the concentrate. After the precipitate thus produced was dried, 250 mg of the red powder was obtained. The powder was dissolved in chloroform, placed on a 4×40 cm column which had been equilibrated with chloroform, rinsed well with chloroform and then fractionated with chloroform-methanol (10:1). The active fraction thus obtained was concentrated under reduced pressure, developed on a TLC plate ("Silica gel 60" manufactured by Merck Co.) with a solvent system of chloroform-methanol-acetic acid-water (40:8:1:1) to collect a reddish orange fraction at an Rf value of about 0.43 by scraping. The fraction thus obtained was eluted, concentrated and then recrystallized from chloroform to obtain 110 mg of R20X.

(4) Preparation of R20X2

After cultivation, the fermentation broth was filtered to separate the bacteria cells and the filtrate. The filtrate was adjusted to pH 2 with 1N HCl and adsorbed on a 10×40 cm column of "Diaion HP20" (manufactured by Mitsubishi Chemical Industries Ltd.). After washing with distilled water and 50% methanol, elution was conducted with methanol. The eluate was concentrated. The concentrate was adjusted to pH 8.5 and extracted three times with a mixture of chloroform-methanol (9:1). The extract was concentrated, and hexane was added in an amount of 6 times that of the concentrate. The precipitate thus produced was dried to obtain 250 mg of a red powder (R20X2 crude product). The crude product of the R20X2 (250 mg) was dissolved in chloroform, placed on a 4×40 cm silica gel column (250 g) which had been equilibrated with chloroform, rinsed well with chloroform and then eluted with chloroform-methanol (10:1). The fraction thus obtained was concentrated under reduced pressure, developed on a TLC plate ("Silica gel 60" manufactured by Merck Co.) with a solvent system of chloroform-methanol-aqueous ammonia (8:2:0.05) to collect an orange fraction at an Rf value of about 0.44 by scraping. The fraction thus obtained was eluted, concentrated and then recrystallized from chloroform to obtain 10 mg of R20X2.

(5) Collection of R20Y5

The filtrate was adjusted to pH 2 with 1N HCl and adsorbed on a 10×40 cm column of "Diaion HP20" (manufactured by Mitsubishi Chemical Industries Ltd.). After washing with distilled water and 50% methanol, elution was conducted with methanol. The eluate was concentrated. The concentrate was adjusted to pH 8.5 and extracted three times with a mixture of chloroform-methanol (9:1). The extract was concentrated, and hexane was added in an amount of 6 times that of the concentrate. The precipitate thus produced was dried to obtain 250 mg of a powder. The product was placed on a 5×40 cm silica gel column ("Silica gel 60" manufactured by Merck Co.) which had been equilibrated with chloroform-methanol-water (70:10:1) to collect a yellow fraction. The fraction thus obtained was concentrated under reduced pressure, developed on a TLC plate ("Silica gel 60" manufactured by Merck Co.) with a solvent system of chloroform-methanol-acetic acid-water (40:8:1:1) to collect a yellow fraction at an Rf value of about 0.50 by scraping. The fraction thus obtained was eluted, concentrated and then recrystallized from chloroform to obtain 1.6 mg of R20Y5.

EXAMPLE 1

40 mg of R20X was dissolved in 3 ml of pyridine, and 150 mg of trifluoroacetic anhydride was added to the mixture. The mixture was stirred at room temperature for 5 hours. Water was added to the mixture, and the resulting mixture was extracted with chloroform. The chloroform layer was concentrated and subjected to thin-layer chromatography with a solvent system of chloroform-methanol (9:1). Collection of a colored portion by scraping gave 16 mg of N-trifluoroacetyl-13-deoxocarminomycin.

Physicochemical properties of N-trifluoroacetyl-13-deoxocarminomycin:
Molecular formula: $C_{28}H_{28}O_9NF_3$,
Molecular weight: 579 (FD-MS),

| Elementary analysis: | Calculated | Found |
|---|---|---|
| C | 58.03 | 58.27 |
| H | 4.87 | 4.65 |
| N | 2.42 | 2.26 |

Specific rotation: $[\alpha]_D^{22} = +289°$, (c=0.1, in 0.01N HCl-MeOH)
Melting point: 141° to 146° C.

| UV-Visible spectrum $\lambda_{max}$ | $(E_{1\ cm}^{1\%})$ |
|---|---|
| 235(686) | 240(725) |
| 255(544) | 298(142) |
| 293(177) | 552(252) |
| 492(293) | (in alkaline methanol) |
| 527(207) | |
| (in acidic methanol) | |

IR spectrum: 1720, 1605 cm$^{-1}$ (KBr)
Proton NMR spectrum $\delta_H$: 1.08(3H, t, J=7.3 Hz, H-14), 1.32(3H, d, J=6.7 Hz, H-6'), 1.50 ~ 1.90(4H, H-13, H-8a, H-2'a), 2.02(1H, dd, J=4.9, 13.5 Hz, H-2'b), 2.37(1H, brd, J=14.7 Hz, H-8'b), 2.57(1H, d, J=19.5 Hz, H-10a), 3.27(1H, dd, J=1.8, 19.5 Hz, H-10b), 3.74(1H, brs, H-4'), 4.21(1H, m, H-3'), 4.37(1H, q, J=6.7 Hz, H-5'), 5.17(1H, brd, J=3.5 Hz, H-7), 5.45(1H, d, J=3.6 Hz, H-1'), 6.67 (1H, d, J=8.5 Hz, NH), 7.30(1H, d, J=8.3 Hz, H-3), 7.70(1H, dd, J=8.3, 8.3 Hz, H-2), 7.87 (1H, d, J=8.3 Hz, H-1).

EXAMPLE 2

Fifty milligram of R20X was dissolved in 6 ml of dioxane, and 170 mg of diglycolic anhydride was added to and refluxed at 120° C. for 4 hours. The mixture was concentrated and subjected to thin-layer silica gel chromatography with a solvent system of chloroform-methanol (4:1). The product fraction was collected by scraping and subjected to gel filtration chromatography on Sephadex LH20 to obtain 30.4 mg of N-carboxymethoxyacetyl-13-deoxocarminomycin.

Physicochemical properties of N-carboxymethoxyacetyl-13-deoxocarminomycin:
Molecular formula: $C_{30}H_{33}O_{13}N$
Molecular weight: 615 (FD-MS)

| Elementary analysis: | Calculated | Found |
|---|---|---|
| C | 58.53 | 58.79 |
| H | 5.40 | 5.51 |
| N | 2.28 | 2.04 |

Specific rotation: $[\alpha]_D^{23} = +185°$, (c=0.08, in 0.01N HCl-MeOH),
Melting point: 170°-174° C. (dec.)

| UV-Visible spectrum $\lambda_{max}$ | $(E_{1\ cm}^{1\%})$ |
|---|---|
| 235(726) | 240(767) |
| 255(576) | 298(150) |
| 293(187) | 550(267) |
| 492(311) | (in alkaline methanol) |
| 527(219) | |
| (in acidic methanol) | |

IR spectrum: 3400, 1730, 1660, 1600 cm$^{-1}$ (KBr)
Proton NMR spectrum $\delta_H$ (in deuterochloroform-deuteromethanol): 1.07(3H, t, J=7.1 Hz, H-14), 1.32(3H, d, J=6.3 Hz, H-6'), 1.68-2.00(5H, H-2', H-13, H-8a), 2.38(1H, d, J=14.0 Hz, H-86), 2.58(1H, d, J=19.0 Hz, H-10a), 3.21(1H, d, J=19.0 Hz, H-10b), 3.71(1H, brs, H-4'), 3.85-4.25(5H, H-3', H-2'', H-4''), 4.30(1H, q, H-5'), 5.15(1H, brs, H-7), 5.44(1H, brs, H-1'), 7.27(1H, d, J=8.2 Hz, H-3), 7.69(1H, dd, J=8.2 Hz, H-2), 7.82(1H, d, J=8.2 Hz, H-1).

EXAMPLE 3

R20X (40 mg) was dissolved in 5 ml of N, N-dimethylformamide, and 46.5 mg of ethyl iodide and 16.2 mg of triethylamine were added to the solution. The mixture was stirred at room temperature for 48 hours. DMF was removed by evaporation, and the residue was subjected to thin-layer silica gel chromatography with a solvent system of chloroform-methanol (9:1). The fractions were collected by scraping to obtain 10.8 mg of N-ethyl-13-deoxocarminomycin from the colored portion at an Rf value of 0.2 and 8.7 mg of N,N-diethyl-13-deoxocarminomycin from the colored portion at an Rf value of 0.3.

Physicochemical properties of N-ethyl-13-deoxocarminomycin:
Molecular formula: $C_{28}H_{33}O_9N$
Molecular weight: 527 (FD-MS)

| Elementary analysis: | Calculated | Found |
|---|---|---|
| C | 63.75 | 63.48 |
| H | 6.30 | 6.49 |
| N | 2.65 | 2.44 |

Specific rotation: $[\alpha]_D^{22} = +287°$, (c=0.1, in 0.01N HCl-MeOH),
Melting point: 126°-130° C. (dec.)

| UV-Visible spectrum $\lambda_{max}$ | $(E_{1\ cm}^{1\%})$ |
|---|---|
| 235(649) | 240(688) |
| 255(529) | 298(132) |
| 293(145) | 554(229) |
| 492(270) | (in alkaline methanol) |
| 527(184) | |
| in acidic methanol) | |

IR spectrum: 3400, 1610 cm$^{-1}$ (KBr)
Proton NMR spectrum (in deuterochloroform): 1.07(3H, t, J=7.3 Hz, H-14), 1.16(3H, t, J=7.3 Hz, H-2''), 1.38(3H, d, J=6.4 Hz, H-6'), 1.65-2.05(5H, H-13, H-8b, H-2'), 2.40(1H, d, J=15.0 Hz, H-8b), 2.57(1H, d, J=19.7 Hz, H-10a), 2.74(2H, m, H-1''), 3.03(1H, m, H-3'), 3.26(1H, J=19.7 Hz, H-10b), 3.77(1H, brs, H-4'), 4.16(1H, q, J=6.4 Hz, H-5'), 5.21(1H, d, J=1.5 Hz, H-7), 5.48(1H, d, J=3.4 Hz, H-1'), 7.30(1H, d, J=8.5 Hz, H-3), 7.70(1H, dd, J=8.5 Hz, H-2), 7.88(1H, d, J=8.5 Hz, H-1).

Physicochemical properties of N,N-diethyl-13-deoxocarminomycin:
Molecular formula: $C_{30}H_{37}O_9N$
Molecular weight: 555 (FD-MS)

| Elementary analysis: | Calculated | Found |
| --- | --- | --- |
| C | 64.85 | 65.10 |
| H | 6.71 | 6.97 |
| N | 2.52 | 2.30 |

Specific rotation: $[\alpha]_D^{22} = +276°$ (c=0.1, in 0.01N HCl-MeOH),
Melting point: 135°–140° C. (dec.)

| UV-Visible spectrum $\lambda_{max}$ | ($E_{1\ cm}^{1\%}$) |
| --- | --- |
| 235(629) | 240(667) |
| 255(513) | 298(128) |
| 293(141) | 554(222) |
| 492(262) | (in alkaline methanol), |
| 527(178) | |
| (in acidic methanol) | |

IR spectrum: 3400, 1610 cm$^{-1}$ (KBr)
Proton NMR spectrum: 1.08(3H, t, J=7.3 Hz, H-14), 1.16(6H, t, J=7.3 Hz, H-2″), 1.38(3H, d, J=6.3 Hz, H-6′), 1.6–2.0(5H, H-13, H-8b, H-2′), 2.38(1H, d, J=14.0 Hz, H-8b), 2.58(1H, d, J=19.0 Hz, H-10a), 2.8–3.4(6H, H-1″, H-3′, H-10b), 3.98(1H, brs, H-4′), 4.08(1H, q, J=6.3 Hz, H-5′), 5.08(1H, brs, H-7), 5.56(1H, d, J=3.0 Hz, H-1′), 7.28(1H, d, J=8.0 Hz, H-3), 7.70(1H, dd, J=8.0, H-2), 7.82(1H, d, J=8.0 Hz, H-1).

EXAMPLE 4

R20X (39.8 mg) was dissolved in a mixture of methanol-chloroform (9:1) and 42.3 mg of benzaldehyde and 10.1 mg of sodium cyanoborohydride were added to the solution. The mixture was stirred at room temperature for 30 minutes and then concentrated. After chloroform extraction, the chloroform layer was concentrated and subjected to thin-layer chromatography with a solvent system of chloroform-methanol (9:1). Collection by scraping gave 19.5 mg of N-benzyl-13-deoxocarminomycin.

Physicochemical properties of N-benzyl-13-deoxocarminomycin:
Molecular formula: $C_{33}H_{35}O_9N$
Molecular weight: 589 (FD-MS)

| Elementary analysis | Calculated | Found |
| --- | --- | --- |
| C | 67.22 | 67.13 |
| H | 5.98 | 5.86 |
| N | 2.38 | 2.32 |

Specific rotation: $[\alpha]_D^{22} = +318°$, (c=0.1, in 0.01N HCl-MeOH),
Melting point: 100°–105° C. (dec.)

| UV-Visible spectrum $\lambda_{max}$ ($E_{1\ cm}^{1\%}$) | |
| --- | --- |
| 235(706) | 240(797) |
| 255(594) | 291(144) |
| 294(183) | 544(253) |
| 492(293) | (in alkaline methanol), |
| 527(210) | |
| (in acidic methanol) | |

IR spectrum: 3400, 1640, 1620 cm$^{-1}$ (KBr)
Proton NMR spectrum (in deuterochloroform): 1.09(3H, t, J=7.3 Hz, H-14), 1.39(3H, d, J=6.7 Hz, H-6′), 1.65–1.90(5H, H-8a, H-13, H-2′), 2.42(1H, d, J=15.3 Hz, H-8b), 2.57(1H, d, J=19.0 Hz, H-10a), 3.02(1H, m, H-3′), 3.26(1H, d, J=19.0 Hz, H-10b), 3.66(1H, d, J=12.8 Hz, H-1″a), 3.68(1H, brs, H-4′), 3.80(1H, d, J=12.8 Hz, H-1″b), 4.16(1H, q, J=6.7 Hz, H-5′), 5.21(1H, brs, H-7), 5.47(1H, d, J=3.8 Hz, H-1′), 7.2–7.3(6H, H-3″, 4″, 5″, 6″, 7″, H-3), 7.70(1H, dd, J=8.0 Hz, H-2), 7.87(1H, d, J=8.0 Hz, H-1).

EXAMPLE 5

In 8 ml of N,N-dimethylformamide was dissolved 40.0 mg of R20X, and 54.5 mg of allyl iodide and 16.2 mg of triethylamine were added to the solution. The N,N-dimethylformamide was removed by evaporation, and 50 ml of water was added to the mixture, which was extracted with 100 ml of chloroform. The chloroform layer was concentrated and subjected to silica gel thin-layer chromatography with a solvent system of chloroform-methanol (9:1). The fractions were collected by scraping to obtain N-allyl-13-deoxocarminomycin at an Rf value of 0.5 and N,N-diallyl-13-deoxocarminomycin at an Rf value of 0.7. These products were individually subjected to gel filtration with Sephadex LH20 to obtain 14.7 mg of N-allyl-13-deoxocarminomycin and 8.3 mg of N,N-diallyl-13-deoxocarminomycin.

Physicochemical properties of N-allyl-13-deoxocarminomycin:
Molecular formula: $C_{29}H_{33}O_9N$
Molecular weight: 539 (FD-MS)

| Elementary analysis | Calculated | Found |
| --- | --- | --- |
| C | 64.55 | 63.29 |
| H | 6.16 | 6.38 |
| N | 2.60 | 2.48 |

Specific rotation: $[\alpha]_D^{22} = +268°$, (c=0.1, in 0.01N HCl-MeOH),
Melting point: 124°–127° C. (dec.)

| UV-Visible spectrum $\lambda_{max}$ ($E_{1\ cm}^{1\%}$) | |
| --- | --- |
| 234(580) | 240(597) |
| 255(445) | 294(121) |
| 292(137) | 554(195) |
| 492(226) | (in acidic methanol)· |
| 526(152) | |
| (in acidic methanol) | |

IR spectrum: 3400, 1600 cm$^{-1}$ (KBr disc)
Proton NMR spectrum (in deuterochloroform): 1.08(3H, t, J=7.3 Hz, H-14), 1.38(3H, d, J=6.3 Hz, H-6′), 1.5–2.0(5H, H-2′, H-13, H-8a), 2.39(1H, d, J=14.0 Hz, H-8b), 2.58(1H, d, J=19.0 Hz, H-10a), 3.05(1H, m, H-3′), 3.25–3.35(3H, H-10b, H-1′), 3.71(1H, brs, H-4′), 4.15(1H, q, J=6.3 Hz, H-5′), 5.13(1H, brd, J=9.5 Hz, H-3″a), 5.19(1H, brd, J=18.2 Hz, H-3″b), 5.22(1H, brs, H-7), 5.48(1H, brs, H-1′), 5.88(1H, m, H-2″), 7.31(1H, d, J=8.0 Hz, H-3), 7.71(1H, dd, J=8.0 Hz, H-2), 7.89(1H, d, J=8.0, H-1).

Physicochemical properties of N,N-diallyl-13-deoxocarminomycin:
Molecular formula: $C_{32}H_{37}O_9N$
Molecular weight: 579 (FD-MS)

| Elementary analysis | Calculated | Found |
| --- | --- | --- |
| C | 66.31 | 66.42 |
| H | 6.43 | 6.59 |

| Elementary analysis | Calculated | Found |
|---|---|---|
| N | 2.42 | 2.21 |

Specific rotation: $[\alpha]_D^{22} = +392°$, (c=0.1, in 0.01N HCl-MeOH),
Melting point: 179°–183° C. (dec.)

| UV-Visible spectrum $\lambda_{max}$ (E$_{1\ cm}^{1\%}$) | |
|---|---|
| 235(644) | 240(709) |
| 255(517) | 293(152) |
| 292(163) | 556(241) |
| 492(261) | (in alkaline methanol), |
| 527(177) | |
| in acidic methanol) | |

IR spectrum: 3400, 1620 cm$^{-1}$ (KBr)
Proton NMR spectrum (in deuterochloroform) $\delta_H$: 1.08(3H, t, J=7.5 Hz, H-14), 1.39(3H, d, J-6.3 Hz, H-6'), 1.65–1.93(5H, H-13, H-8a, H-2'), 2.40(1H, d, J=14.3 Hz, H-8b), 2.59(1H, d, J=19.3 Hz, H-10a), 2.82(1H, m, H-3'), 3.19(4H, m, H-1"), 3.27(1H, d, J=19.3 Hz, H-10b), 3.68(1H, brs, H-4'), 4.10(1H, q, J=6.3 Hz, H-5'), 5.29(2H, brd, J=9.5 Hz, H-3"a), 5.30(2H, brd, J=16.7 Hz, H-3"b), 5.21(1H, brs, H-7), 5.51(1H, brs, H-1'), 5.73(2H, m, H-2"), 7.32(1H, d, J=7.6 Hz, H-3), 7.71(1H, dd, J=7.6 Hz, H-2), 7.90(1H, d, J=7.6 Hz, H-1).

EXAMPLE 6

In 30 ml of ethanol was dissolved 200 mg of pyruvic aldehyde dimethyl acetal, and 34 mg of sodium cyanoborohydride was added to the solution. The mixture was stirred at room temperature for 2 hours, neutralized with 1N HCl, concentrated. The residue was extracted with chloroform, and the organic layer was dehydrated and then concentrated. The concentrate was dissolved in the mixed solution of acetone-water (20:1). A catalytic amount of p-toluenesulfonic acid was added to the solution, and the mixture was stirred at 40° C. for 150 minutes and neutralized with a cationic ion exchanger IRA-410. The supernatant was concentrated to obtain 60.1 mg of 2-hydroxypropanal. The product was dissolved in methanol, and 95.8 mg of R20X and 36.2 mg of sodium cyanoborohydride were added sequentially to the solution. The mixture was stirred for 30 minutes and then concentrated. The concentrate was subjected to silica gel thin-layer chromatography with a solvent system of chloroform-methanol (5:1), and the colored portion was collected by scraping, eluted, concentrated and further subjected to gel filtration on Sephadex LH20 with a solvent system of chloroform-methanol (1:1) to obtain 46.4 mg of N-(2"-hydroxypropyl)-13-deoxocarminomycin.

Physicochemical properties of N-(2"-hydroxypropyl)-13-deoxocarminomycin:
Molecular formula: C$_{29}$H$_{35}$O$_{10}$N
Molecular weight: 557 (FD-MS)

| Elementary analysis | Calculated | Found |
|---|---|---|
| C | 62.47 | 62.12 |
| H | 6.33 | 6.59 |
| N | 2.51 | 2.38 |

Specific rotation: $[\alpha]_D^{22} = +326°$, (c=0.1, in 0.01N HCl-MeOH),
Melting point: 134°–138° C. (dec.)

| UV-Visible spectrum $\lambda_{max}$ | |
|---|---|
| 235(729) | 240(770) |
| 255(565) | 299(144) |
| 294(162) | 556(263) |
| 492(308) | (in alkaline methanol), |
| 527(208) | |
| in acidic methanol) | |

IR spectrum: 3400, 1600 cm$^{-1}$ (KBr).
Proton NMR spectrum (in deuterochloroform): 1.09(3H, t, J=7.3 Hz, H-14, 1.13(3H, d, J=6.0 Hz, H-3"), 1.37(3H, d, J=6.0 Hz, H-6"), 1.60–1.95(5H, H-8a, H-13, H-2'), 2.39(1H, d, J=15.5 Hz, H-8b), 2.50(1H, ddd, J=10.0, 12.5, 12.5 Hz, H-1"a), 2.57(1H, d, J=19.0 Hz, H-10a), 2.77(1H, ddd, J=3.5, 12.5, 12.5 Hz), 2.96(1H, m, H-3'), 3.26(1H, d, J=19.0 Hz, H-10b), 3.73(1H, brs, H-4'), 3.86(1H, m, H-2"), 4.18(1H, q, J=6.0 Hz, H-5'), 5.20(1H, brs, H-7), 5.48(1H, brs, H-1'), 7.30(1H, dd, J=2.0, 8.0 Hz, H-3), 7.70(1H, ddd, J=2.0, 8.0, 8.0 Hz, H-2), 7.88(1H, dd, J=2.0, 8.0 Hz, H-1).

EXAMPLE 7

In a mixture of methanol-water (10:1) was dissolved 100.7 mg of R20X, and 90.8 mg of D-(+)-glyceraldehyde and 25.3 mg of sodium cyanoborohydride were added to the solution. The mixture thus formed was stirred for 2 hours. The reaction was concentrated and then extracted with a mixed solvent of chloroform-methanol (10:1). The organic layer was dried, concentrated and subjected to silica gel thin-layer chromatography with a solvent system of chloroform-methanol (5:1). The colored fraction was collected by scraping, concentrated and subjected to gel filtration on Sephadex LH20 with a solvent system of chloroform-methanol (1:1) to obtain 24.2 mg of N-[(2"S)-2",3"-dihydroxypropyl]-13-deoxocarminomycin.

In the same manner, 19.0 mg of [(2"R)-2",3"-dihydroxypropyl]-13-deoxocarminomycin was obtained from 110.0 mg of R20X, 99.2 mg of L-(−)-glyceraldehyde and 27.7 mg of sodium cyanoborohydride.

Physicochemical properties of N-[(2"S)-2",3"-dihydroxypropyl]-13-deoxocarminomycin:
Molecular formula: C$_{29}$H$_{35}$O$_{11}$N
Molecular weight: 573 (FD-MS)

| Elementary analysis | Calculated | Found |
|---|---|---|
| C | 60.73 | 60.80 |
| H | 6.15 | 6.32 |
| N | 2.44 | 2.30 |

Specific rotation: $[\alpha]_D^{23} = +292°$, (c=0.05, in 0.01N HCl-MeOH),
Melting point: 154°–159° C. (dec.)

| UV-Visible spectrum $\lambda_{max}$ (E$_{l\ cm}^{1\%}$) | |
|---|---|
| 235(502) | 239(482) |
| 255(401) | 299(96) |
| 293(114) | 551(200) |
| 492(206) | (in alkaline methanol) |
| 526(144) | |
| (in acidic methanol) | |

IR spectrum: 3400, 1600 cm$^{-1}$ (KBr).

Physicochemical properties of N-[(2"R)-2",3"-dihydroxypropyl]-13-deoxocarminomycin:
  Molecular formula: $C_{29}H_{35}O_{11}N$
  Molecular weight: 573 (FD-MS)

| Elementary analysis | Calculated | Found |
| --- | --- | --- |
| C | 60.73 | 60.54 |
| H | 6.15 | 6.29 |
| N | 2.44 | 2.51 |

Specific rotation: $[\alpha]_D^{22} = +296°$, (c=0.1, in 0.01N HCl-MeOH),
Melting point: 146°–151° C. (dec.)

| UV-Visible spectrum | |
| --- | --- |
| 235(578) | 240(609) |
| 255(451) | 299(116) |
| 293(131) | 557(219) |
| 492(240) | (in alkaline methanol) |
| 527(161) | |
| (in acidic methanol) | |

IR spectrum: 3400, 1600 cm$^{-1}$ (KBr).

EXAMPLE 8

In 15 ml of methanol was dissolved 93.7 mg of R20X, and 20.8 mg of acetol and 22.6 mg of sodium cyanoborohydride were added to the solution. The mixture was stirred at room temperature for 30 minutes. The reaction mixture was concentrated and then subjected to silica gel thin-layer chromatography with a solvent system of chloroform-methanol (5:1). The colored portion was collected by scraping, eluted with a mixture of chloroform-methanol and subjected to gel filtration on Sephadex LH20 with a solvent system of chloroform-methanol (1:1) to obtain 35.0 mg of N-(1"-hydroxy-2"-propyl)-13-deoxocarminomycin.

Physicochemical properties of N-(1"-hydroxy-2"-propyl)-13-deoxocarminomycin:
  Molecular formula: $C_{29}H_{35}O_{10}N$
  Molecular weight: 557 (FD-MS)

| Elementary analysis | Calculated | Found |
| --- | --- | --- |
| C | 62.47 | 62.19 |
| H | 6.33 | 6.58 |
| N | 2.51 | 2.40 |

Specific rotation: $[\alpha]_D^{22} = +298°$, (c=0.1, in 0.01N HCl-MeOH),
Melting point: 134°–139° C. (dec.)

| UV Visible spectrum | |
| --- | --- |
| 235(674) | 240(744) |
| 255(540) | 298(144) |
| 293(159) | 558(254) |
| 492(274) | (in alkaline methanol) |
| 527(193) | |
| (in acidic methanol) | |

IR spectrum: 3400, 1600 cm$^{-1}$ (KBr).

EXAMPLE 9

In 10 ml of methanol was dissolved 91.2 mg of R20X, and 32.4 mg of pyruvic aldehyde dimethyl acetal and 23.0 mg of sodium cyanoborohydride were added to the solution. The mixture was stirred at room temperature for 2 hours, concentrated and subjected to silica gel thin-layer chromatography. After development with a solvent system of chloroform-methanol (5:1), the colored portions at Rf values of 0.6 and 0.65 were respectively collected by scraping. These portions were eluted with a mixture of chloroform-methanol and subjected to gel filtration on Sephadex LH20 with a solvent system of chloroform-methanol (1:1). From the fraction at a Rf value of 0.65 was obtained 30.1 mg of N-(1",1"-dimethoxy-2"-propyl)-13-deoxocarminomycin A, and from the fraction at an Rf value of 0.60 was obtained 28.8 mg of N-(1",1"-dimethoxy-2"-propyl)-13-deoxocarminomycin B. A and B are isomers having different configurations at 2"-position.

Physicochemical properties of N-(1",1"-dimethoxy-2"-propyl)-13-deoxocarminomycin A and B:
  Molecular formula: A, B $C_{31}H_{38}O_{11}N$
  Molecular weight:
  A 600 (FD-MS)
  B 600 (FD-MS)
  Specific rotation: A $[\alpha]_D^{22} = +270°$ (c=0.1, in 0.01 N HCl-MeOH),
  Specific rotation: B $[\alpha]_D^{22} = +277°$ (c=0.1, in 0.01 N HCl-MeOH),
  Melting point: A 96°–102° C. (dec.)
  Melting point: B 101°–104° C. (dec.)

| | UV-Visible spectrum | |
| --- | --- | --- |
| A | 235(636) | 240(700) |
| | 255(513) | 290(152) |
| | 292(170) | 556(238) |
| | 492(262) | (in alkaline methanol) |
| | 527(177) | |
| | (in methanol) | |
| B | 235(846) | 240(896) |
| | 254(662) | 298(180) |
| | 293(199) | 553(309) |
| | 492(345) | (in alkaline methanol) |
| | 526(232) | |
| | (in methanol) | |

IR spectrum:
A 3400, 1605 cm$^{-1}$
B 3400, 1605 cm$^{-1}$ (KBr).

EXAMPLE 10

In a mixture of acetonitrile-water (1:1) was dissolved 50.8 mg of R20X, and 0.5 ml of 40% glycolic acid and 25.2 mg of sodium cyanoborohydride were added to the solution. The mixture was stirred at room temperature for 8 hours. The precipitate produced was separated by filtration and dissolved with a mixture of chloroform-methanol (10:1), and subjected to gel filtration on Sephadex LH20 with a solvent system of chloroform-methanol (1:1) to obtain 23.0 mg of N-carboxymethyl-13-deoxocarminomycin.

Physicochemical properties of N-carboxymethyl-13-deoxocarminomycin:
  Molecular formula: $C_{28}H_{31}O_{11}N$
  Molecular weight: 557 (FD-MS)

| Elementary analysis | Calculated | Found |
| --- | --- | --- |
| C | 60.32 | 60.46 |
| H | 5.60 | 5.69 |
| N | 2.51 | 2.43 |

Specific rotation: $[\alpha]_D^{22} = +219°$ (c=0.1, in 0.01 N HCl-MeOH),

Melting point: 144°–150° C. (dec.)

| UV Visible spectrum | |
|---|---|
| 235(698) | 240(715) |
| 255(543) | 299(139) |
| 290(162) | 552(247) |
| 494(289) | (in alkaline methanol), |
| 527(190) | |
| (in methanol) | |

IR spectrum: 3400, 1700, 1600 cm$^{-1}$

Proton NMR spectrum (in deuteromethanol): 1.10(3H, t, J=7.3 Hz, H-14), 1.32(3H, d, J=6.2 Hz, H-6'), 1.5–2.1(5H, H-13, H-8a, H-2'), 2.30(1H, d, J=14.9 Hz, H-8b), 2.60(1H, d, J=19.0 Hz, H-10a), 3.10(1H, d, J=19.0 Hz, H-10b), 3.0–3.8(2H, H-3', H-4'), 4.20(1H, q, J=6.2 Hz, H-5'), 4.70(2H, s, H-1''), 5.06(1H, brs, H-7), 5.50(1H, brs, H-1'), 7.30(1H, dd, J=2.0, 8.2 Hz, H-3), 7.70(1H, dd, J=8.2, 8.2 Hz, H-2), 7.78(1H, d, J=2.0, 8.2 Hz, H-1)

EXAMPLE 11

In methanol was dissolved 40.5 mg of R20X, and 33.7 mg of cyclopentanone and 10 mg of sodium cyanoborohydride were added to the solution. The mixture was stirred at room temperature for 2 hours, concentrated and subjected to silica gel thin-layer chromatography with a solvent system of chloroform-methanol (10:1) for development. The colored fraction was collected by scraping, eluted with a mixture of chloroform-methanol and subjected to gel filtration on Sephadex LH20 with a solvent system of chloroform-methanol (1:1) to obtain 30.4 mg of N-cyclopentyl-13-deoxocarminomycin.

Physicochemical properties of N-cyclopentyl-13-deoxocarminomycin:

Molecular formula: $C_{31}H_{37}O_9N$
Molecular weight: 567 (FD-MS)

| Elementary analysis | Calculated | Found |
|---|---|---|
| C | 65.60 | 65.41 |
| H | 6.57 | 6.78 |
| N | 2.47 | 2.21 |

Specific rotation: $[\alpha]_D^{23}$ = +232° (c=0.2, in 0.01 N HCl-MeOH),
Melting point: 132°–135° C. (dec.)

| UV-Visible spectrum | |
|---|---|
| 235(834) | 239(826) |
| 255(667) | 293(196) |
| 293(227) | 547(296) |
| 492(342) | (in alkaline methanol) |
| 527(237) | |
| (in acidic methanol) | |

IR spectrum: 3400, 1600 cm$^{-1}$

Proton NMR spectrum (in deuterochloroform): 1.10(3H, t, J=7.3 Hz, H-13), 1.38(3H, d, J=6.0 Hz, H-6'), 1.40–2.20(14H, H-2', H-8a, H-13, H-2'', H-5'', H-3'', H-4'', H-1''), 2.37(1H, d, J=13.0 Hz, H-8b), 2.52(1H, d, J=19.0 Hz, H-10b), 3.19(2H, H-10b, H-3''), 3.80(1H, brs, H-4'), 4.22(J=6.0 Hz, H-5'), 5.11(1H, brs, H-7), 5.46(1H, brs, H-1'), 7.22(1H, d, J=8.0, H-3), 7.68(1H, dd, J=8.0, 8.0 Hz, H-2), 7.77(1H, d, J=8.0 Hz, H-1).

EXAMPLE 12

In methanol was dissolved 50.7 mg of R20X, and 50.0 mg of tetrahydro-4H-pyran-4-one and 10 mg of sodium cyanoborohydride were added to the solution. The mixture was stirred at room temperature for 150 minutes, concentrated and subjected to silica gel thin-layer chromatography with a solvent system of chloroform-methanol (10:1). The colored fraction was collected by scraping, eluted with a mixture of chloroform-methanol and subjected to gel filtration on Sephadex LH20 with a solvent system of chloroform-methanol (1:1) to obtain 40.8 mg of N-(4''-tetrahydropyranyl)-13-deoxocarminomycin. Physicochemical properties of N-(4''-tetrahydropyranyl)-13-deoxocarminomycin:

Molecular formula: $C_{31}H_{37}O_{10}N$
Molecular weight: 583 (FD-MS)

| Elementary analysis | Calculated | Found |
|---|---|---|
| C | 63.80 | 63.54 |
| H | 6.39 | 6.62 |
| N | 2.40 | 2.18 |

Specific rotation: $[\alpha]_D^{23}$ = +404° (c=0.29, in 0.01 N HCl-MeOH),
Melting point: 132°–135° C.

| UV-Visible spectrum ($E_{1\ cm}^{1\%}$) | |
|---|---|
| 235(922) | 240(967) |
| 254(722) | 293(227) |
| 293(246) | 553(321) |
| 492(382) | (in alkaline methanol) |
| 527(266) | |
| (in acidic methanol) | |

IR spectrum: 3400, 1600 cm$^{-1}$

Proton NMR spectrum $\delta_H$: 1.10(3H, t, J=7.8 Hz, H-14), 1.30–1.60(2H, m, H-2'), 1.38(3H, d, J=6.8 Hz, H-6'), 1.65–1.95(7H, m, H-8a, H-13, H-3'', H-5''), 2.41(1H, d, J=13.6 Hz, H-8b), 2.53(1H, d, J=18.8 Hz, H-10a), 2.74(1H, m, H-4''), 3.10(1H, m, H-3'), 3.22(1H, d, J=18.8 Hz, H-10b), 3.25–4.0(4H, H-2'', H-6''), 3.60(1H, brs, H-4'), 4.19(1H, q, H-5'), 5.14(1H, brs, H-7), 5.45(1H, d, J=3.6 Hz, H-1'), 7.25(1H, d, J=8.0 Hz, H-3), 7.64(1H, dd, J=8.0, 8.0 Hz, H-2), 7.69(1H, d, J=8.0 Hz, H-1).

EXAMPLE 13

In 30 ml of pyridine was dissolved 1 g of 4-piperidone hydrochloride, and 10 ml of trifluoroacetic anhydride was added on an ice bath. After addition, the mixture was stirred at room temperature for 15 hours, diluted with water and extracted with chloroform. The chloroform layer was washed with 0.01 N aqueous NaOH, 0.01 N aqueous HCl and water, dried and then concentrated to dryness to obtain 0.93 g of N-trifluoroacetyl-4-piperidone (m.p. 68° C., IR: 1730, 1720, 1690 cm$^{-1}$).

In methanol was dissolved 50.2 mg of R20X, and 36.3 mg of N-trifluoroacetyl-4-piperidone and 12.6 mg of sodium cyanoborohydride were added to the solution. The mixture was stirred at room temperature for 4 hours, concentrated and subjected to silica gel thin-layer chromatography with a solvent system of chloroform-methanol (9:1). The colored portion was collected by scraping, eluted with a mixture of chloroform-methanol, concentrated and subjected to gel filtration on Sephadex LH20 with a solvent system of chloroform-methanol (1:1) to obtain 36.5 mg of N-(1″-trifluoroacetyl-4″-piperidinyl)-13-deoxocarminomycin.

In the same manner, 153 mg of R20X2 was dissolved in methanol, and 111 mg of N-trifluoroacetyl-4-piperidone and 37.4 mg of sodium cyanoborohydride were added to the solution. After the reaction, 95.0 mg of N-(1″-trifluoroacetyl-4″-piperidinyl)-13-deoxo-10-hydroxycarminomycin was obtained by the same purification procedure as described above.

Further, by dissolving 24.3 mg of N-(1″-trifluoroacetyl-4″-piperidinyl)-13-deoxocarminomycin in 2 ml of methanol, adding 0.2 N aqueous Ba(OH)$_2$ solution and stirring at room temperature for 2 hours, 7.8 mg of N-(piperidinyl)-13-deoxocarminomycin was obtained.

Physicochemical properties of N-(1″-trifluoroacetyl-4″-piperidinyl)-13-deoxocarminomycin:

Molecular formula: $C_{33}H_{37}O_{10}N_2F_3$
Molecular weight: 678 (FD-MS)

| Elementary analysis | Calculated | Found |
| --- | --- | --- |
| C | 58.40 | 58.32 |
| H | 5.50 | 5.73 |
| N | 4.13 | 4.01 |

Specific rotation: $[\alpha]_D^{23} = +366°$ (c=0.28, in 0.01 N HCl-MeOH),
Melting point: 136°–139° C.

| UV-Visible spectrum | |
| --- | --- |
| 235 (903) | 240 (913) |
| 255 (699) | 299 (183) |
| 293 (210) | 551 (330) |
| 492 (378) | (in alkaline methanol) |
| 527 (256) | |
| (in acidic methanol) | |

IR spectrum: 3400, 1700, 1600 cm$^{-1}$ (KBr).

Proton NMR spectrum $\delta_H$: 1.10(3H, t, J=7.8 Hz, H-14), 1.15–1.40(2H, m, H-2′), 1.38(3H, d, J=6.5 Hz, H-6′), 1.60–1.98(7H, m, H-8a, H-13, H-3″, H-5″), 2.42(1H, d, J=15 Hz, H-8b), 2.53(1H, dd, J=19 Hz, 2.5 Hz, H-10a), 2.78–3.15(4H, m, H-3′, H-2″a, H-6″a, H-4″), 3.23(1H, d, J=19 Hz, H-10b), 3.55(1H, brs, H-4′), 3.8–4.35(3H, m, H-5′, H-2″b, H-6″b), 5.15(1H, brs, H-7), 5.45(1H, brs, H-1′), 7.23(1H, d, J=8.0 Hz, H-3), 7.65(1H, dd, J=8.0, 8.0 Hz, H-2), 7.80(1H, d, J=8.0 Hz, H-1).

Physicochemical properties of k-(1″-trifluoroacetyl-4″-piperidinyl)-13-deoxo-10-hydroxycarminomycin:

Molecular formula: $C_{33}H_{37}O_{10}N_2F_3$
Molecular weight: 694 (FD-MS)

| Elementary analysis | Calculated | Found |
| --- | --- | --- |
| C | 57.06 | 56.82 |
| H | 5.37 | 5.49 |
| N | 4.03 | 3.95 |

Specific rotation: $[\alpha]_D^{24} = +466°$ (c=0.5, in 0.01 N HCl-MeOH),
Melting point: 128°–131° C.

| UV-Visible spectrum | |
| --- | --- |
| 235 (660) | 239 (654) |
| 254 (399) | 297 (129) |
| 292 (139) | 552 (225) |

| UV-Visible spectrum | |
| --- | --- |
| 494 (249) | (in alkaline methanol) |
| 528 (164) | |
| (in acidic methanol) | |

IR spectrum: 3500, 1700, 1600 cm$^{-1}$ (KBr)

Proton NMR spectrum $\delta_H$: 1.12(3H, t, J=7.3 Hz, H-14), 1.36(3H, d, J=6.2 Hz, H-6′), 1.20–1.95(6H, H-13, H-2′, H-3″, H-5″), 2.15(1H, dd, J=3.5, 14.8 Hz, H-8a), 2.24(1H, d, J=14.8 Hz, H-8b), 2.8–3.2(6H, H-3′, H-4″, H-2″a, H-6″a), 3.56(1H, brs, H-4′), 3.80–4.32(6H, H-2″b, H-6″b, H-5′), 4.85(1H, s, H-10), 5.12(1H, brs, H-7), 5.45(1H, brs, H-1′), 7.30(1H, d, J=8.0 Hz, H-3), 7.74(1H, dd, J=8.0, 8.0 Hz, H-2), 7.82(1H, d, J=8.0 Hz, H-1).

Physicochemical properties of N-(4″-piperidinyl)-13-deoxocarminomycin:

Molecular formula: $C_{31}H_{38}O_9N_2 \cdot HCl$
Molecular weight: 582 (FD-MS)
Specific rotation: $[\alpha]_D^{22} = +305.2°$ (c=0.1, in 0.01 N HCl-MeOH),
Melting point: 139°–142° C.

| UV-Visible spectrum ($E_{1\,cm}^{1\%}$) | |
| --- | --- |
| 235 (594) | 240 (623) |
| 255 (463) | 298 (121) |
| 294 (137) | 555 (215) |
| 492 (250) | (in alkaline methanol) |
| 527 (170) | |
| (in acidic methanol) | |

IR spectrum: 3400, 1600 cm$^{-1}$

Proton NMR spectrum $\delta_H$ (in deuterochloroform-deuteromethanol): 1.10(3H, t, J=7.3 Hz, H-13), 1.34(3H, d, J=6.5 Hz, H-6′), 1.65–2.35(8H, H-8, H-13, H-3″, H-5″), 2.64(1H, d, J=19 Hz, H-10a), 3.1–3.25(2H, H-4″, H-10b), 3.3–3.8(5H, H-3′, H-2″, H-6″), 3.92(1H, brs, H-4′), 4.22(1H, q, J=6.5 Hz, H-5′), 5.16(1H, brs, H-7), 5.53(1H, brs, H-1′), 7.34(1H, d, J=8.0 Hz, H-3), 7.75(1H, dd, J=8.0, 8.0 Hz, H-2), 7.90(1H, d, J=8.0 Hz, H-1).

EXAMPLE 14

10 g of 3-pentanone and a catalytic amount of p-toluene sulfonic acid was added in 10 ml of methylorthoformate and stirred at room temperature for 2 hours. The mixture was added to a solution of 5 g of D-mannitol in 50 ml of N,N-dimethylformamide. The mixture was stirred for 6 hours, neutralized with IRA-410 and concentrated. Water was added to the concentrate, and the mixture was extracted with chloroform. The chloroform layer was concentrated and subjected to silica gel chromatography with a solvent system of chloroform-methanol (100:1) to obtain 2.93 g of the diethylidene derivative of D-mannitol. The product was dissolved in 11 ml of a methanol-water (9:1) solution, and 3.20 g of periodic acid was added to the solution. The mixture was stirred for 5 hours and then filtrated. Water was added and the mixture was extracted with chloroform. The chloroform layer was washed with water, dehydrated, concentrated and subjected to a silica gel chromatography with a solvent system of chloroform-methanol (100:1) to obtain 1.87 g of 2″,3″-diethylidenedioxypropanal.

Next, 84.1 mg of R20X was dissolved in methanol, and 36.9 mg of 2″,3″-diethylidenedioxypropanal and 21.2 mg of sodium cyanoborohydride were added to the solution. The mixture was stirred at room temperature for 30 minutes, concentrated and developed by silica gel thin-layer chromatography with a solvent system of chloroform-methanol (10:1). The colored portion was collected by scraping, eluted with a mixture of chloroform-methanol and then subjected to gel filtration on Sephadex LH20 with a solvent system of chloroform-methanol (1:1) to obtain 13.5 mg of N-[(2″S)-2″, 3″-diethylidenedioxypropyl]-13-deoxocarminomycin.

Physicochemical properties of N-[(2″S)-2″, 3″diethylidene-dioxypropyl]-13-deoxocarminomycin:
Molecular formula: $C_{34}H_{43}O_{11}N$
Molecular weight: 641 (FD-MS)

| Elementary analysis | Calculated | Found |
|---|---|---|
| C | 63.64 | 62.48 |
| H | 6.75 | 6.59 |
| N | 2.18 | 2.07 |

Specific rotation: $[\alpha]_D^{22} = +270°$ (c=0.1, in 0.01 N HCl-MeOH),
Melting point: 6°–71° C. (dec.)

| UV-Visible spectrum | |
|---|---|
| 235 (613) | 240 (633) |
| 255 (480) | 299 (124) |
| 293 (142) | 551 (218) |
| 492 (254) | (in alkaline methanol) |
| 526 (167) | |
| (in acidic methanol) | |

IR spectrum: 3450, 1600 cm$^{-1}$ (KBr)
Proton NMR spectrum: 0.84(6H, t, J=7.6 Hz, H-6″, 8″), 1.10(3H, t, J=7.3 Hz, H-14), 1.40(3H, d, J=6.5 Hz, H-6′), 1.40–2.00(9H, H-2′, H-13, H-5″, H-7″, H-8a), 2.40(1H, d, J=14.5 Hz, H-8b), 2.5–3.1(4H, H-10b, H-1″, H-3′), 3.30(1H, d, J=19.0 Hz, H-10b), 3.62(1H, brs, H-4′), 3.5–4.3(4H, H-3″a, H-3″b, H-2″, H-5′), 5.24(1H, brs, H-7), 5.48(1H, brs, H-1′), 7.32(1H, d, J=8.0 Hz, H-3), 7.72(1H, dd, J=8.0, 8.0 Hz, H-2), 7.94(1H, d, J=8.0 Hz, H-1).

EXAMPLE 15

10 g of 4-heptanone and a catalytic amount of p-toluenesulfonic acid were added to 10 ml of methyl outhoformate and stirred at room temperature for 2 hours. The mixture was added to a solution of 5.0 g of D-mannitol in 50 ml at N,N-dimethylformamide. The reaction mixture was stirred for 6 hours, neutralized with a cation exchange resin IRA-410 and concentrated. Water was added to the concentrate, and the mixture was extracted with chloroform. The organic layer was concentrated and subjected to silica gel chromatography with a solvent system of chloroform-methanol (100:1) to obtain 1.30 g of the bis dipropylidene derivative of D-mannitol. The product was dissolved in 11 ml of a methanol-water (9:1) solution, and 1.11 g of periodic acid was added to the solution. The mixture was stirred for 5 hours and then filtrated. Water was added and the mixture was extracted with chloroform. The chloroform layer was washed several times with water, concentrated and subjected to a silica gel column chromatography with a solvent system of chloroform-methanol (100:1) to obtain 0.50 g of 2″,3″-dipropylidenedioxy-1″-propanal.

Next, 103.2 mg of R20X was dissolved in methanol, and 57.7 mg of 2″,3″-dipropylidenedioxy-1″-propanal and 26.0 mg of sodium cyanoborohydride were added to the solution. The mixture was stirred at room temperature for 30 minutes, concentrated and developed by silica gel thin-layer chromatography with a solvent system of chloroform-methanol (10:1). The colored portion was collected by scraping, eluted with a mixture of chloroform-methanol and then subjected to gel filtration on Sephadex LH20 with a solvent system of chloroform-methanol (1:1) to obtain 13.5 mg of N-[(2″S)-2″,3″-dipropylidenedioxypropyl]-13-deoxocarminomycin.

Physicochemical properties of N-[(2″S)-2″, 3″-dipropylidenedioxypropyl]-13-deoxocarminomycin:
Molecular formula: $C_{36}H_{47}O_{11}N$
Molecular weight: 669 (FD-MS)

| Elementary analysis | Calculated | Found |
|---|---|---|
| C | 64.56 | 65.68 |
| H | 7.07 | 7.23 |
| N | 2.09 | 1.92 |

Specific rotation: $[\alpha]_D^{22} = +362°$ (c=0.1, in 0.01 N HCl-MeOH),
Melting point: 66°–70° C.

| UV-Visible spectrum | |
|---|---|
| 235 (678) | 240 (700) |
| 255 (531) | 299 (137) |
| 293 (157) | 551 (241) |
| 492 (281) | (in alkaline methanol) |
| 526 (185) | |
| (in acidic methanol) | |

IR spectrum: 3400, 1600 cm$^{-1}$ (KBr)
Proton NMR spectrum: 0.84(6H, t, J=7.6 Hz, H-7″, 10″), 1.09(3H, t, J=7.3 Hz, H-14), 1.38(3H, d, J=6.3 Hz, H-6′), 1.40–2.00(13H, H-2′, H-13, H-5″, H-6″, H-8″, H-9″, H-8a), 2.40(1H, d, J=14.3 Hz, H-8b), 2.5–3.1(4H, H-10a, H-1″, H-3′), 3.30(1H, d, J=19.0 Hz, H-10b), 3.60(1H, brs, H-4′), 3.5–4.3(4H, H-3″a, H-3″b, H-2″, H-5), 5.22(1H, brs, H-7), 5.46(1H, brs, H-1′), 7.32(1H, d, J=8.2 Hz, H-3), 7.70(1H, dd, J=8.2, 8.2 Hz, H-2), 7.94(1H, d, J=8.2 Hz, H-1).

EXAMPLE 16

3 ml of cyclopentanone and a catalytic amount of p-toluenesolfonic acid were added to 10 ml of methyl orthoformate and the mixture was stirred for 4 hours. Then the mixture was added to a solution of 5.0 g of D-mannitol in 50 ml of N,N-dimethylformamide. The reaction mixture was stirred for 6 hours, neutralized with a cation exchange resin IRA-410 and concentrated. Water was added to the concentrate, and the mixture was extracted with chloroform. The organic layer was concentrated, and subjected to silica gel column chromatography with a solvent system of chloroform-methanol (100:1) to obtain 0.96 g of the bis cyclopentylidene derivative of D-mannitol. The product was dissolved in 50 ml of a methanol-water (9:1) solution, and 0.57 g of periodic acid was added to the solution. The mixture was stirred for 6 hours and then filtrated. Water was added and the mixture was extracted with chloroform. The chloroform layer was washed several times with water, concentrated and subjected to a silica gel column chromatography with a solvent system of chloroform-methanol (100:1) to obtain 0.26 g of 2″,3‴-cyclopentylidenedioxy-1‴-propanal.

Next, 110 mg of R20X was dissolved in 12 ml of methanol, and 51.9 mg of 2″,3‴-cyclopentylidenedioxy-1‴-propanal and 27.8 mg of sodium cyanoborohydride were added to the solution. The mixture was stirred at room temperature, concentrated and developed by silica gel thin-layer chromatography with a solvent system of chloroform-methanol (10:1). The colored portion was collected by scraping, eluted with a mixture of chloroform-methanol and then subjected to gel filtration on Sephadex LH20 with a solvent system of chloroform-methanol (1:1) to obtain 58.5 mg of N-[(2″S)-2″,3‴-cyclopentylidenedioxypropyl]-13-deoxocarminomycin.

Physicochemical properties of N-[(2″S)-2″,3‴-cyclopentylidenedioxypropyl]-13-deoxocarminomycin:

Molecular formula: $C_{34}H_{41}O_{11}N$
Molecular weight: 639 (FD-MS)

| Elementary analysis | Calculated | Found |
|---|---|---|
| C | 63.84 | 63.69 |
| H | 6.51 | 6.58 |
| N | 2.19 | 2.16 |

Specific rotation: $[\alpha]_D^{22} = +318°$ (c=0.1, in 0.01 N HCl-MeOH),
Melting point: 96°–99° C. (dec.)

| UV-Visible spectrum | |
|---|---|
| 235 (639) | 240 (659) |
| 255 (500) | 299 (129) |
| 293 (148) | 551 (227) |
| 492 (265) | (in alkaline methanol) |
| 527 (174) | |
| (in acidic methanol) | |

IR spectrum: 3400, 1600 cm$^{-1}$ (KBr)

Proton NMR spectrum: (in deuterochloroform) $\delta_H$: 1.10(3H, t, J=7.3 Hz, H-14), 1.38(3H, d, J=6.0 Hz, H-6′), 1.50–1.95(13H, H-2′, H-13, H-8a, H-5″, H-6″, H-7″, H-8″), 2.40(1H, d, J=14.3 Hz, H-8b), 2.5–3.1(4H, H-10a, H-1″, H-3′), 3.30(1H, d, J=19.0 Hz, H-10b), 3.60(1H, brs, H-4′), 3.5–4.3(4H, H-3″a, H-3″b, H-2‴, H-5), 5.22(1H, brs, H-7), 5.46(1H, brs, H-1′), 7.32(1H, d, J=8.2 Hz, H-3), 7.70(1H, dd, J=8.2, 8.2 Hz, H-2), 7.94(1H, d, J=8.2 Hz, H-1).

EXAMPLE 17

9.24 g of cycloheptanone and a catalytic amount of p-toluenesulfonic acid were added to 10 ml of methyl orthoformate and the mixture was stirred for 5 hours. Then the mixture was added to a solution of 5.0 g of D-mannitol in 50 ml of N,N-dimethylformamide. The reaction mixture was stirred for further 5 hours, neutralized with a cation exchange resin IRA-410 and concentrated. Water was added to the concentrate, and the mixture was extracted with chloroform, dried and subjected to silica gel column chromatography with a solvent system of chloroform-methanol (100:1) to obtain 4.65 g of the bis cycloheptylidene derivative of D-mannitol. The product was dissolved in 50 ml of a methanol-water (9:1) solution, and 0.87 g of periodic acid was added to the solution. The mixture was stirred for 20 hours and then filtrated. Water was added and the mixture was extracted with chloroform. The chloroform layer was washed several times with water, concentrated and subjected to a silica gel column chromatography with a solvent system of chloroform-methanol (100:1) to obtain 3.92 g of 2″,3‴-cycloheptylidenedioxy-1‴-propanal.

Next, 108.0 mg of R20X was dissolved in 15 ml of methanol, and 59.7 mg of 2″,3‴-cycloheptylidenedioxy-1‴-propanal and 27.2 mg of sodium cyanoborohydride were added to the solution. The mixture was stirred at room temperature, concentrated and developed by silica gel thin-layer chromatography with a solvent system of chloroform-methanol (10:1). The colored portion was collected by scraping, eluted with a mixture of chloroform-methanol and then subjected to gel filtration on Sephadex LH20 with a solvent system of chloroform-methanol (1:1) to obtain 24.7 mg of N-[(2″S)-2″,3‴-cycloheptylidenedioxypropyl]-13-deoxocarminomycin.

Physicochemical properties of N-[(2″S)-2″,3‴-cycloheptylidenedioxypropyl]-13-deoxocarminomycin:

Molecular formula: $C_{36}H_{45}O_{11}N$
Molecular weight: 667 (FD-MS)

| Elementary analysis | Calculated | Found |
|---|---|---|
| C | 64.75 | 64.69 |
| H | 6.79 | 6.85 |
| N | 2.10 | 2.03 |

Specific rotation: $[\alpha]_D^{22} = +393°$ (c=0.1, in 0.01 N HCl-MeOH),
Melting point: 96°–100° C. (dec.)

| UV-Visible spectrum | |
|---|---|
| 235 (625) | 240 (645) |
| 255 (489) | 299 (126) |
| 293 (145) | 552 (222) |
| 492 (254) | (in alkaline methanol) |
| 526 (170) | |
| (in acidic methanol) | |

IR spectrum: 3400, 1600 cm$^{-1}$ (KBr)

Proton NMR spectrum (in deuterochloroform) $\delta_H$: 1.08(3H, t, J=7.3 Hz, H-14), 1.38(3H, d, J=6.0 Hz, H-6′), 1.50–1.95(19H, H-8a, H-13, H-2′, H-5″10″), 2.40(1H, d, J=14.3 Hz, H-8b), 2.50–3.10(4H, H-10a, H-1″, H-3′), 3.30(1H, d, J=19.0 Hz, H-10b), 3.60(1H, brs, H-4′), 3.50–4.30(4H, H-3″a, H-3″b, H-2‴, H-5′), 5.24(1H, brs, H-7), 5.46(1H, brs, H-1′), 7.32(1H, d, J=8.2 Hz, H-3), 7.70(1H, dd, J=8.2, 8.2 Hz, H-1), 7.94(1H, d, J=8.2 Hz, H-1).

EXAMPLE 18

In 10 ml of methanol was dissolved 50 mg of R20X, and 200 mg of 25% glutaric dialdehyde solution and 10.8 mg of sodium cyanoborohydride were added to the solution. The mixture was stirred at room temperature for 30 minutes. The reaction mixture obtained was concentrated and subjected to silica gel thin-layer chromatography with a solvent system of chloroform-methanol (10:1). The colored fraction was collected by scraping, eluted with a mixture of chloroform-methanol and subjected to gel filtration on a column of Sephadex LH20 with a solvent system of chloroform-methanol (1:1) to obtain 48.4 mg of 3′-deamino-3′-(1″-piperidino)-13-deoxocarminomycin.

Physicochemical properties of 3'-deamino-3'-(1''-piperidino)-13-deoxocarminomycin:
Molecular formula: $C_{31}H_{37}O_9N$
Molecular weight: 567 (FD-MS)

| Elementary analysis | Calculated | Found |
|---|---|---|
| C | 65.60 | 65.38 |
| H | 6.57 | 6.86 |
| N | 2.47 | 2.19 |

Specific rotation: $[\alpha]_D^{22} = +318°$ (c=0.1, in 0.01 N HCl-MeOH),
Melting point: 124°–128° C. (dec.)

| UV-Visible spectrum ($E_{1\ cm}^{1\%}$) | |
|---|---|
| 235 (616) | 240 (653) |
| 255 (489) | 299 (130) |
| 294 (142) | 551 (224) |
| 492 (260) | (in alkaline methanol) |
| 526 (176) | |
| (in acidic methanol) | |

IR spectrum: 3400, 1605 cm$^{-1}$.
Proton NMR spectrum (in deuterochloroform) $\delta_H$: 1.09(3H, t, J=7.3 Hz, H-13), 1.40(3H, d, J-6.0 Hz, H-6'), 1.7–1.95(9H, H-8a, H-13, H-3'', H-4'', H-5''), 2.3–2.6(6H, H-8b, H-10a, H-2'', H-6''), 3.21(1H, d, J=18.5 Hz, H-10b), 3.77(1H, brs, H-4'), 4.14(1H, q, J=6.0 Hz, H-5'), 5.15(1H, brs, H-7), 5.48(1H, brs, H-1'), 7.26(1H, d, J=8.0 Hz, H-3), 7.67(1H, dd, J=8.0, 8.0 Hz, H-2), 7.78(1H, d, J=8.0 Hz, H-1).

EXAMPLE 19

In 10 ml of pyridine was dissolved 0.5 g of diallylamine hydrochloride, and 1.0 g of acetic anhydride was added to the solution. The mixture was stirred at room temperature for 10 hours. Water was added to the mixture and the mixture was extracted with chloroform. The chloroform layer was washed with 0.01 N aqueous HCl solution, 1% aqueous sodium bicarbonate solution and finally with water, and concentrated to obtain 0.47 g of N-acetyldiallylamine [IR: 1640 cm$^{-1}$, $^1$H-NMR $\delta_H$ 2.08 (3H), 3.94(4H), 5.16(4H), 5.76(2H)].

In 150 ml of methylene chloride was dissolved N-acetyldiallylamine, and the solution was treated with ozone at $-65°$ C. for 10 hours. After 10 hours, 20 ml of dimethylsulfide was added to the mixture, and the mixture was stirred at room temperature for further 10 hours. The solvent was removed under reduced pressure, and a solution of 40 mg of R20X in 5 ml of methanol was added to the residue. Then, 10.1 mg of sodium cyanoborohydride was further added to the mixture and the mixture was stirred at room temperature for 1 hour. Water was added to the reaction mixture, and the mixture thus formed was extracted with chloroform. The chloroform layer was dried, concentrated and subjected to silica gel thinlayer chromatography with a solvent system of chloroform-methanol (10:1). The colored band at an Rf value of ca. 0.4 was scraped off, eluted with a mixed solvent of chloroform-methanol and concentrated. The concentrate was subjected to gel filtration on Sephadex LH20 with a solvent system of chloroform-methanol (1:1) and the fraction thus obtained was concentrated. The concentrate was dissolved in a small amount of chloroform, and 20 ml of hexane was added to the solution. The precipitate thus formed was collected by centrifugation and dried to obtain 12.4 mg of 3'-deamino-3'-(1''-acetyl-4'-piperazinyl)-13-deoxocarminomycin. In the same manner, 25.4 mg of 3'-deamino-3'-(1''-acetyl-4''-piperadinyl)-13-deoxo-10-hydroxycarminomycin was obtained from 110 mg of R20X2.

Physicochemical properties of 3'-deamino-3'-(1''-acetyl-4'-piperazinyl)-13-deoxocarminomycin:
Molecular formula: $C_{32}H_{38}O_{10}N_2$
Molecular weight: 610 (FD-MS)

| Elementary analysis | Calculated | Found |
|---|---|---|
| C | 62.94 | 61.70 |
| H | 6.27 | 6.15 |
| N | 4.59 | 4.44 |

Specific rotation: $[\alpha]_D^{22} = +313°$ (c=0.1, in 0.01 N HCl-MeOH),
Melting point: 146°–151° C. (dec.)

| UV-Visible spectrum | |
|---|---|
| 235 (673) | 240 (698) |
| 254 (390) | 297 (152) |
| 292 (146) | 552 (260) |
| 495 (244) | (in alkaline methanol) |
| 528 (165) | |
| (in acidic methanol) | |

IR spectrum: 3400, 1730, 1620 cm$^{-1}$ (KBr)
Proton NMR spectrum: 1.08(3H, t, J=7.8 Hz, H-14), 1.38(3H, d, J=6.3 Hz, H-6'), 1.5–2.0(5H, H-8a, H-2', H-13), 2.00(3H, s, CoCH$_3$), 2.2–2.6(6H, H-3'', H-5'', H-8b, H-10a), 3.22(1H, d, J=19.0 Hz, H-10b), 3.20–3.60(4H, H-2'', H-6''), 3.70(1H, brs, H-4'), 4.14(1H, q, J=6.3 Hz, H-5'), 5.14(1H, brs, H-7), 5.48(1H, brs, H-1'), 7.24(1H, d, J=8.0 Hz, H-3), 7.64(1H, dd, J=8.0, 8.0 Hz, H-2), 7.80(1H, d, J=8.0, H-1).

Physicochemical properties of 3'-deamino-3'-(1''-acetyl-4''-piperazinyl)-13-deoxo-10-hydroxycarminomycin:
Molecular formula: $C_{32}H_{38}O_{11}N_2$
Molecular weight: 626 (FD-MS)

| Elementary analysis | Calculated | Found |
|---|---|---|
| C | 61.33 | 61.15 |
| H | 6.11 | 6.28 |
| N | 4.47 | 4.32 |

Specific rotation: $[\alpha]_D^{24} = +440°$ (c=0.13, in 0.01 N HCl-MeOH),
Melting point: 143°–147° C.

| UV-Visible spectrum | |
|---|---|
| 235 (641) | 238 (598) |
| 254 (371) | 297 (118) |
| 292 (132) | 552 (210) |
| 494 (234) | (in alkaline methanol) |
| 528 (154) | |
| (in acidic methanol) | |

IR spectrum: 3400, 1730, 1600 cm$^{-1}$ (KBr)
Proton NMR spectrum: 1.12(3H, t, J=7.2 Hz, H-14), 1.40(3H, d, J=6.5 Hz, H-6'), 1.73–1.91(4H, H-13, H-2'), 2.13(1H, dd, J=3.8, 14.2 Hz, H-8a), 2.25(1H, d, J=14.2 Hz, H-8b), 2.38–2.62(4H, H-2'', 4''), 3.3–3.73(4H, H-1'', H-5"), 3.92(1H, brs, H-4'), 4.10(1H, q, J=6.5 Hz, H-5'), 4.90(1H, s, H-10), 5.14(1H, dd, J=1 Hz, 3.8 Hz, H-7), 5.51(1H, brs, H-1'), 7.32(1H, d, J=8.2 Hz, H-3), 7.72(1H, dd, J=8.2, 8.2 Hz, H-2), 7.87(1H, dd, J=8.2, H-1).

EXAMPLE 20

In 100 ml of pyridine was dissolved 5.08 g of D-(+)-xylose, and 20 ml of acetic anhydride was added to the solution on an ice bath. The mixture was stirred at room temperature for 5 hours. Water was added to the mixture and the mixture was extracted with chloroform. The chloroform layer was washed with 0.1 N HCl, 1% sodium bicarbonate solution and finally with water, dehydrated and concentrated to obtain 11.32 g of the tetra-o-acetyl derivative of xylose. The product was dissolved in 100 ml of methylene chloride, and 17.28 g of 25% hydrobromide/acetic acid solution was added and stirred. After 4 hours, water was added to the mixture, and the mixture was extracted with methylene chloride. The methylene chloride layer was washed twice with 1% sodium bicarbonate solution and further with water. The organic layer was concentrated and crystallized from a solvent system of diethyl ether-hexane to obtain 8.47 g of 2,3,4-tri-O-acetyl-α-D-xylopyranosyl bromide.

$[\alpha]_D^{24} = +181°$ (c=0.5, in chloroform),
Melting point: 92° C.,
Proton NMR spectrum $\delta_H$ 2.05 (6H, s, OAc), 2.10 (3H, s, OAc), 3.89 (1H, dd, J=11.0, 11.0 Hz, H-5a), 4.05(1H, dd, J=5.0, 11.0 Hz, H-5b), 4.78(1H, dd, J=1.8, 11.0 Hz, H-2), 5.05(1H, ddd, J=5.0, 11.0, 11.0 Hz, H-4), 5.58(1H, dd, J=11.0, 11.0 Hz, H-3), 6.58(1H, d, J=1.8 Hz, H-1).

In acetonitrile was dissolved 3 g of 2,3,4-tri-O-acetyl-α-D-xylopyranosyl bromide, and 2.88 g of dry sodium azide was added to the solution. The mixture was stirred at 60° C. for 4 hours. Water was added to the reaction and the mixture was extracted with chloroform. The chloroform layer was washed with water, dehydrated and subjected to silica gel column chromatography with a solvent system of chloroform-acetone (100:1) to obtain 1.36 g of 2,3,4-tri-O-acetyl-1-azido-1-deoxy-β-D-xylopyranose.

Specific rotation: $[\alpha]_D = -123°$
Melting point: 76° C.
IR spectrum: 2130, 1750 cm$^{-1}$
Proton NMR spectrum $\delta_H$ 2.04(3H, s, OAc), 2.05(3H, s, OAc), 2.08(3H, s, OAc), 3.44(1H, dd, J=10.0, 13.2 Hz, H-5ax), 4.22(1H, dd, J=5.0, 13.2 Hz, H-5eq), 4.64(1H, d, J=9.0 Hz, H-1), 4.88(1H, dd, J=9.0, 9.0 Hz, H-2), 4.98(1H, ddd, J=5.0, 9.0, 10.0 Hz, H-4), 5.20(1H, dd, J=9.0, 9.0 Hz, H-3).

In 20 ml of ethyl acetate was dissolved 0.73 g of 2,3,4-tri-O-acetyl-1-azido-1-deoxy-β-D-xylopyranose, and 65 mg of 10% Pd/C was added to the solution. Then the solution was stirred in a hydrogen atmosphere for 2 hours. The Pd/C was removed by filtration, and the filtrate was concentrated. To the concentrate was added 20 ml of pyridine, 3 ml of acetic anhydride and then 10 mg of 4-dimethylaminopyridine, and the mixture was stirred for 16 hours. Water was added to the reaction, and the mixture was extracted with chloroform. The chloroform layer was washed with 0.1 N HCl solution, 1% sodium bicarbonate solution and finally with water, dehydrated and concentrated. The residue was subjected to silica gel column chromatography with a system of chloroform-acetone (100:1) to obtain 0.4 mg of 1-acetamido-2,3,4-tri-O-acetyl-1-deoxy-β-D-xylopyranose.

Specific rotation: $[\alpha]_D^{21} = +21°$ (c=0.9, in methanol)
Melting point: 170° C.
IR spectrum: 1760, 1740, 1660 cm$^{-1}$ (KBr)
Proton NMR spectrum: 2.00(3H, s, OAc), 2.05(3H, s, OAc), 2.06(3H, s, OAc), 2.10(3H, s, NAc), 3.35(1H, dd, J=11.0, 11.0 Hz, H-5ax), 4.06(1H, dd, J=5.5, 11.0 Hz, H-5eq), 4.87(1H, dd, J=10.0, 10.0 Hz, H-2), 4.98(1H, ddd, J=5.5, 10.0, 11.0 Hz, H-4), 5.15(1H, dd, J=10.0, 10.0 Hz, H-3), 5.30(1H, dd, J=10.0, 10.0 Hz, H-2), 6.39(1H, d, J=10.0, NH).

In 10 ml of methanol was dissolved 380 mg of 1-acetamide-2,3,4-tri-O-acetyl-1-deoxy-β-D-xylopyranose, and 3 mg of sodium methoxide was added to the solution. The mixture was stirred at room temperature for 14 hours, then neutralized with 1 N HCl, and 10 ml of water was added to the mixture. Further, 780 mg of sodium periodate was added, and the mixture was stirred for 3 hours. The reaction mixture was filtered, and the filtrate was concentrated. Methanol was added to the residue, and the resulting precipitate was separated by filtration. The filtrate was concentrated to afford 290 mg of 3-acetamido-2,6-dihydroxydioxane. In methanol was dissolved 50.2 mg of R20X, and 145 mg of 3-acetamido-2,6-dihydroxydioxane and 13.8 mg of sodium cyanoborohydride were sequentially added. The mixture was stirred at room temperature for 1 hour, then concentrated and subjected to silica gel thin-layer chromatography. The colored portion was scraped off, eluted with a mixed solvent of chloroform-methanol, concentrated and subjected to gel filtration on Sephadex LH20 with a solvent system of chloroform-methanol (1:1) to obtain 27.9 mg of 3'-deamino-3'-[(2"R)-2'-acetamido-4"-morpholino]-13-deoxocarminomycin.

In the same manner, 38.7 mg of 3'-deamino-3'-[(2"R)-2"-acetamido-4"-morpholino]-13-deoxo-10-hydroxycarminomycin was obtained from 110 mg of R20X2 and 145 mg of 3-acetamido-2,6-dihydroxydioxane.

Physicochemical properties of 3'-deamino-3'-[(2"R)-2"-acetamido-4"-morpholino]-13-deoxocarminomycin:
Molecular formula: $C_{32}H_{38}O_{11}N_2$
Molecular weight: 626 (FD-MS)

| Elementary analysis | Calculated | Found |
|---|---|---|
| C | 61.33 | 61.09 |
| H | 6.11 | 6.23 |
| N | 4.47 | 4.38 |

Specific rotation: $[\alpha]_D^{24} = +326°$ (c=0.2, in 0.01 N HCl-MeOH),
Melting point: 158°–161° C. (dec.)

| UV-Visible spectrum | |
|---|---|
| 235(626) | 240(680) |
| 255(487) | 297(130) |
| 293(140) | 554(232) |
| 492(253) | (in alkaline methanol) |
| 528(170) | |
| (in acidic methanol) | |

IR spectrum: 3450, 1670, 1600 cm$^{-1}$ (KBr)
Proton NMR spectrum: (in deuterochloroform) 1.09(3H, t, J=7.4 Hz, H-14), 1.38(3H, d, J=6.2 Hz, H-6'), 1.65–1.90(4H, H-13, H-2'), 2.00(3H, s, NAc), 2.1–2.90(7H, H-8a, 8b, 10a, H-3″, 5″), 3.28(1H, d, J=19.0 Hz, H-10b), 3.68(1H, m, H-6″a), 3.70(1H, brs, H-4′), 3.83(1H, m, H-6″b), 4.15(1H, q, J=6.2 Hz, H-5′), 5.22(1H, brs, H-7), 5.32(1H, ddd, J=2.5, 8.2, 8.2 Hz, H-2″), 5.53(1H, brs, H-1′), 6.23(1H, d, J=8.2 Hz, -NH-), 7.31(1H, d, J=8.3 Hz, H-3), 7.71(1H, dd, J=8.3, 8.3 Hz, H-2), 7.88(1H, d, J=8.3 Hz, H-1).

Physicochemical properties of 3′-deamino-3′-[(2″R)-2″-acetamido-4″-morpholino]-13-deoxo-10-hydroxycarminomycin:

Molecular formula: $C_{32}H_{38}O_{12}N_2$
Molecular weight: 642 (FD-MS)

| Elementary analysis: | Calculated | Found |
|---|---|---|
| C | 59.81 | 59.63 |
| H | 5.96 | 6.08 |
| N | 4.36 | 4.24 |

Specific rotation: $[\alpha]_D^{24} = +347°$ (c=0.2, in 0.01 N HCl-MeOH),

Melting point: 170°–174° C. (dec.)

| UV-Visible spectrum | |
|---|---|
| 235(605) | 240(562) |
| 255(352) | 297(113) |
| 292(123) | 554(184) |
| 494(224) | (in alkaline methanol) |
| 528(148) | |
| (in acidic methanol) | |

IR spectrum: 3450, 1660, 1600 cm$^{-1}$ (KBr).

Proton NMR spectrum: (in deuterochloroform) 1.12(3H, t, J=7.3 Hz, H-14), 1.37(3H, d, J=6.2 Hz, H-6′), 1.70–1.90(4H, H-2′, H-13), 1.98(3H, s, NAc), 2.15(1H, dd, J=4.5, 14.8 Hz, H-8a), 2.22(1H, d, J=14.8 Hz, H-8b), 2.25–2.70(4H, H-3″, H-5″), 3.65(1H, m, H-6″a), 3.73(1H, brs, H-4′), 3.80(1H, m, H-6″b), 4.09(1H, q, J=6.2 Hz, H-5′), 4.85(1H, s, H-10), 5.12(1H, brs, H-7), 5.30(1H, m, H-2′), 5.49(1H, brs, H-1′), 7.29(1H, d, J=8.0 Hz, H-3), 7.70(1H, dd, J=8.0, 8.0 Hz), 7.81(1H, d, J=8.0 Hz).

EXAMPLE 21

In 20 ml of methanol was dissolved 2.65 g of D-xylose, and a catalytic amount of p-toluenesulfonic acid was added. The mixture was stirred at 40° C. for 3 hours, neutralized with a cation exchange resin IRA-410 and concentrated to obtain 3.09 g of methyl-D-xyloside. In 50 ml of water was dissolved 3.09 g of methyl-D-xyloside, 10.0 of sodium periodate was added, and the mixture was stirred at room temperature for 4 hours.

The aqueous layer was concentrated, and a large amount of methanol was added to the concentrate. The precipitate thus formed was filtered and the filtrate was concentrated and subjected to silica gel column chromatography with a solvent system of chloroform-methanol (1:1) to obtain a compound represented by the formula (III):

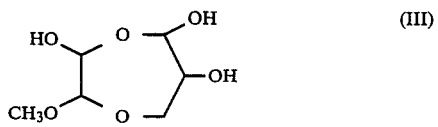

(III)

In methanol was dissolved 101.1 mg of the compound, and 67.3 mg of R20X and then 84.7 mg of sodium cyanoborohydride were added to the solution. The mixture was stirred at room temperature for 40 minutes, concentrated and subjected to silica gel thin-layer chromatography with a solvent system of chloroform-methanol (10:1). A scraped portion was eluted with a mixed solvent of chloroform-methanol and concentrated. The concentrate was further subjected to silica gel thin-layer chromatography with a solvent system of chloroform-methanol (10:1). A scraped colored fraction at an Rf value of 0.6 produced 22.7 mg of 3′-deamino-3′-(6″-hydroxy-2″-methoxy-4″-perhydroxazepinyl)-13-deoxocarminomycin A. Colored fraction at the Rf value of 0.55 produced 24.7 mg of 3′-deamino-3′-(6″-hydroxy-2″-methoxy-4″-perhydroxazepinyl)-13-deoxocarminomycin B. A and B are isomers at the 2″-position.

Physicochemical properties of 3′-deamino-3′-(6″-hydroxy-2″-methoxy-4″-perhydrooxazepinyl)-13-deoxocarminomycin A, B:

Molecular formula: A, B $C_{32}H_{39}O_{12}N$
Molecular weight:
A: 629 (FD-MS)
B: 629 (FD-MS)

| Elementary analysis: | Calculated | Found |
|---|---|---|
| A: | | |
| C | 61.04 | 60.78 |
| H | 6.24 | 6.45 |
| N | 2.22 | 2.02 |
| B: | | |
| C | 61.04 | 60.29 |
| H | 6.24 | 6.32 |
| N | 2.22 | 2.07 |

Specific rotation: A: $[\alpha]_D^{22} = +247°$ (c=0.12, in 0.01 N HCl-MeOH),

Specific rotation: B: $[\alpha]_D^{22} = +355°$ (c=0.1, in 0.01 N HCl-MeOH),

Melting point:
A: 137°–140° C.
B: 139°–143° C.

| UV-Visible Spectrum | |
|---|---|
| A: | |
| 235(628) | 240(682) |
| 254(491) | 297(133) |
| 293(144) | 554(235) |
| 493(256) | (in alkaline methanol) |
| 526(173) | |
| (in acidic methanol) | |
| B: | |
| 235(614) | 240(643) |
| 255(474) | 300(167) |
| 294(135) | 556(221) |
| 493(258) | (in alkaline methanol) |
| 526(174) | |
| (in acidic methanol) | |

IR spectrum:
A: 3400, 1600 cm$^{-1}$ (KBr)
B: 3400, 1600 cm$^{-1}$ (KBr)

Proton NMR spectrum: (in deuterochloroform) $\delta_H$
A: 1.08(3H, t, J=7.9, H-14), 1.39(3H, d, J=6.5 Hz, H-6′), 1.63–1.86(5H, H-2′, H-8a, H-13), 1.92(1H, dd, J=7.4, 10.9 Hz, H-3″a), 2.08(1H, dd, J=11.0, 11.0 Hz, H-5″a), 2.40(1H, d, J=15.2 Hz, H-8b), 2.43(1H, m, H-3′), 2.55(1H, d, J=18.9 Hz, H-10a), 2.66(1H, d, J=11.0 Hz, H-5″b), 3.02(1H, d, J=7.4 Hz, H-3″b), 3.24(1H, d, J=18.9 Hz, H-10b), 3.49(3H, s, OMe), 3.60(1H, m, H-6″), 3.65-3.72(3H, H-7″, H-4′), 4.14(1H, q, H-5′), 4.57(1H, d, J=7.1 Hz, H-2″), 5.19(1H, brs, H-7), 5.50(1H, brs, H-1′), 7.28(1H, d, J=8.0 Hz, H-3), 7.70(1H, dd, J=8.0, 8.0 Hz, H-2), 7.84(1H, d, J=8.0 Hz, H-1).

B: 1.08(3H, t, J=7.3 Hz, H-14), 1.39(3H, d, J=6.7 Hz, H-6′), 1.60-1.90(5H, H-13, H-8, H-2′), 2.06(1H, dd, J=11.0, 11.0 Hz, H-5″a), 2.13(1H, dd, J=1.8, 11.6 Hz, H-3″a), 2.48(2H, H-8a, H-3′), 2.56(1H, d, J=18.9 Hz, H-10a), 2.77(1H, d, J=10.9 Hz, H-5″b), 3.05(1H, d, J=11.6 Hz, H-3″b), 3.25(1H, d, J=18.9 Hz, H-10b), 3.35(3H, s, OMe), 3.52(1H, dd, J=4.9, 11.6 Hz, H-7a), 3.61(1H, dd, J=3.6, 11.6 Hz, H-7b), 3.68(1H, brs, H-4′), 3.98(1H, m, H-6″), 4.12(1H, q, J=6.7 Hz, H-5′), 4.66(1H, s, H-2″), 5.09(1H, brs, H-7), 5.50(1H, brs, H-1′), 7.30(1H, d, J=7.9 Hz, H-3), 7.71(1H, dd, J=7.9, 7.9 Hz, H-2), 7.85(1H, d, J=7.9 Hz, H-1).

EXAMPLE 22

In 20 ml of N-N-dimethylformamide was dissolved 155.9 mg of R20X, and 133.3 mg of 3,4-dihydro-2-pyran and 107.7 mg of paratoluenesulfonic acid were added. The mixture was stirred at room temperature for 24 hours.

After completion of the reaction, the mixture was poured into 50 ml of 0.1 N sodium bicarbonate and extracted with chloroform. The chloroform and N,N-dimethylformamide were removed by evaporation, and the residue was subjected to silica gel thin-layer chromatography with a solvent system of chloroform-methanol (10:1). Colored fractions at the Rf values of 0.55 and 0.50 were respectively scraped off, eluted and concentrated. The concentrates were subjected to gel filtration on Sephadex LH20 with a solvent system of chloroform-methanol (1:1). The fraction at the Rf value of 0.55 produced 16.5 mg of 4′-tetrahydropyranyl-13-deoxocarminomycin A, and the fraction at an Rf value of 0.50 produced 17.8 mg of 4′-tetrahydropyranyl-13-deoxocarminomycin B. A and B are the isomers at 1‴-position.

Physicochemical properties of 4′-tetrahydropyranyl-13-deoxocarminomycin A, B:

Molecular formula: A, B $C_{31}H_{37}O_{10}N$
Molecular weight:
A: 583 (FD-MS)
B: 583 (FD-MS)

| Elementary analysis: | Calculated | Found |
|---|---|---|
| A: | | |
| C | 63.80 | 63.59 |
| H | 6.39 | 6.45 |
| N | 2.40 | 2.28 |
| B: | | |
| C | 63.80 | 63.62 |
| H | 6.39 | 6.56 |
| N | 2.40 | 2.31 |

Specific rotation: A: $[\alpha]_D^{22} = +315°$
Specific rotation: B: $[\alpha]_D^{22} = =334°$ (c=0.1, in methanol),
Melting point:
A: 124°–126° C.
B: 144°–148° C.

| UV-Visible spectrum | |
|---|---|
| A: | |
| 235(631) | 240(647) |
| 255(491) | 299(126) |
| 293(146) | 552(223) |
| 492(261) | (in alkaline methanol) |
| 526(172) | |
| (in acidic methanol) | |
| B: | |
| 235(627) | 240(646) |
| 255(490) | 299(126) |
| 293(145) | 552(222) |
| 492(260) | (in alkaline methanol) |
| 526(170) | |
| (in acidic methanol) | |

IR spectrum:
A: 3400, 1600 cm$^{-1}$
B: 3400, 1600 cm$^{-1}$

Proton NMR spectrum: (in deuterochloroform) $\delta_H$

A: 1.08(3H, t, J=7.9 Hz, H-14), 1.28(3H, d, J=6.4 Hz, H-6′), 1.40-2.00(11H, H-8a, H-13, H-2′, H-2″, H-3″, H-4″), 2.40(1H, d, J=15.0 Hz, H-8b), 2.56(1H, d, J=19.0 Hz, H-10a), 3.08(1H, m, H-3′), 3.28(1H, d, J=19.0 Hz, H-10b), 3.50(1H, m, H-5″a), 3.65(1H, brs, H-4′), 3.96(1H, m, H-5″b), 4.18(1H,q, J=6.4 Hz, H-5′), 4.70(1H, brdd, J=3.0, 5.4 Hz, H-1″), 5.10(1H, brs, H-7), 5.30(1H, brs, H-1′), 7.30(1H, d, J=8.0 Hz, H-3), 7.70(1H, dd, J=8.0, 8.0 Hz), 7.88(1H, d, J=8.0 Hz, H-1).

B: 1.08(3H, t, J=8.0 Hz, H-14), 1.30(3H, d, J=6.4 Hz, H-6′), 1.40-2.00(11H, H-8a, H-13, H-2′, H-2″, H-3″, H-4″), 2.38(1H, d, J=14.6 Hz, H-8b), 2.50(1H, d, J=19.0 Hz, H-10a), 3.24(1H, d, J=19.0 Hz, H-10b), 3.62(1H, brs, H-4′), 3.10-4.10(3H, H-3′, H-5″), 4.26(1H, q, J=6.4 Hz, H-5′), 4.40(1H, m, H-1″), 5.12(1H, brs, H-7), 5.50(1H, brs, H-1′), 7.26(1H, d, J=8.0 Hz, H-3), 7.70(1H, dd, J=8.0, 8.0 Hz, H-2), 7.84(1H, d, J=8.0 Hz, H-1).

EXAMPLE 23

In methanol was dissolved 30.4 mg of 4′-O-tetrahydropyranyl-13-deoxocarminomycin A, and 31.3 mg of 2,6-dihydroxydioxan and 6.6 mg of sodium cyanoborohydride were added. The mixture was stirred at room temperature for 60 minutes. The reaction mixture was concentrated and subjected to silica gel thin-layer chromatography with a solvent system of chloroform-methanol (20:1). The colored fractions was scraped off, eluted with a mixed solvent of chloroform-methanol and subjected to gel filtration on Sephadex LH20 with a solvent system of chloroform-methanol (1:1) to give 14.9 mg of 3′-deamino-3′-(4″-morpholino)-4′-O-tetrahydropyranyl-13-deoxocarminomycin A.

In the same manner, starting from 37.8 mg of 4′-O-tetrahydropyranyl-13-deoxocarminomycin B, 15.9 mg of 3′-deamino-3′-(4″-morpholino)-4′-O-tetrahydropyranyl-13-deoxocarminomycin B was obtained. A and B are stereosiomers at 1‴-position.

Physicochemical properties of 3′-deamino-3′-(4″-morpholino)-4′-O-tetrahydropyranyl-13-deoxocarminomycin A, B:

Molecular formula: A, B $C_{35}H_{43}O_{11}N$
Molecular weight:
A: 653 (FD-MS)
B: 653 (FD-MS)

| Elementary analysis: | Calculated | Found |
|---|---|---|
| A: | | |
| C | 64.31 | 64.23 |
| H | 6.63 | 6.38 |
| N | 2.14 | 2.07 |
| B: | | |
| C | 64.31 | 64.09 |
| H | 6.63 | 6.56 |
| N | 2.14 | 2.10 |

Specific rotation:
A: $[\alpha]_D^{22} = +362°$
B: $[\alpha]_D^{22} = +315°$ (c=0.1, in methanol),
Melting point:
A: 94°–98° C.
B: 117°–120° C.

| UV-Visible spectrum | |
|---|---|
| A: | |
| 235(582) | 240(597) |
| 255(453) | 299(116) |
| 293(135) | 552(206) |
| 492(241) | (in alkaline methanol) |
| 526(159) | |
| (in acidic methanol) | |
| B: | |
| 235(598) | 240(613) |
| 255(465) | 299(119) |
| 293(139) | 552(212) |
| 492(248) | (in alkaline methanol) |
| 526(163) | |
| (in acidic methanol) | |

IR spectrum:
A: 3400, 1600 cm$^{-1}$
B: 3400, 1600 cm$^{-1}$

Proton NMR spectrum: (in deuterochloroform) $\delta_H$
A: 1.08(3H, t, J=7.9 Hz, H-14), 1.36(3H, d, J=6.8 Hz, H-6'), 1.5–2.1(11H, H-13, H-8a, H-2', H-2''', H-3''', H-4'''), 2.35–2.55(6H, H-8b, H-3', H-3'', H-5''), 2.58(1H, d, J=19.0 Hz, H-10a), 3.27(1H, d, J=19.0 Hz, H-10b), 3.45(1H, m, H-5'''a), 3.62(4H, m, H-2'', H-6''), 3.92(1H, brs, H-4'), 3.97(1H, m, H-5'''b), 4.12(1H, q, J=6.8 Hz, H-5'), 4.32(1H, s, 9-OH), 5.09(1H, ddd, J=<1, 3.0, 5.5 Hz, H-1'''), 5.22(1H, brs, H-7), 5.54(1H, d, J=3.6 Hz, H-1'), 7.31(1H, d, J=8.5 Hz, H-3), 7.70(1H, dd, J=8.5, 8.5 Hz, H-2), 7.89(1H, d, J=8.5 Hz, H-1).

B: 1.08(1H, t, J=7.9 Hz, H-14), 1.28(3H, d, J=6.7 Hz, H-b'), 1.5–2.1(11H, H-8a, H-13, H2', H-2''', H-3''', H-4''''), 2.35–2.55(6H, H-8b, H-3', H-3'', H-5''), 2.58(1H, d, J=18.9 Hz, H-10a), 3.26(1H, d, J=18.9, H-10b), 3.42(1H, m, H-5'''a), 3.64(1H, m, H-2'', H-6''), 3.80(1H, brs, H-4'), 4.07(1H, q, J=6.7 Hz, H-5'), 4.09(1H, m, H-5'''b), 4.31(1H, s, 9-OH), 4.68(1H, br dd, J=3.7, 3.7 Hz, H-1'''), 5.22(1H, brs, H-7), 5.54(1H, d, J=3.0 Hz, H-1'), 7.31(1H, d, J=8.3 Hz, H-3), 7.71(1H, dd, J=8.3, 8.3 Hz, H-2), 7.88(1H, d, J=8.3 Hz, H-1).

EXAMPLE 24

In 300 ml of acetone was dissolved 2.05 g of 3'-deamino-3'-(4''-morpholino)-13-deoxo-10-hydroxy carminomycin, and 5 ml of Jones reagent (prepared by dissolving 70 g of chromium trioxide in 500 ml of water and adding 61 ml of sulfuric acid thereto) was added. The mixture was stirred at room temperature for 2 hours. The reaction mixture was concentrated to 50 ml of its volume, and 300 ml of water was added to the concentrate. The mixture was extracted five times with 300 ml of chloroform, and the chloroform layer was washed with water, dehydrated and concentrated. The residue was subjected to silica gel column chromatography, and eluted sequentially with a mixed solvent of toluene-acetone (50:1, 20:1, 10:1 and 5:1) to obtain 270.1 mg of 3'-deamino-3'-(4''-morpholino)-13-deoxo-10-oxocarminomycin.

Physicochemical properties of 3'-deamino-3'-(4''-morpholino)-13-deoxo-10-oxocarminomycin:
Molecular formula: $C_{30}H_{33}O_{11}N$
Molecular weight: 583 (FD-MS)

| Elementary analysis: | Calculated | Found |
|---|---|---|
| C | 61.74 | 61.48 |
| H | 5.70 | 5.95 |
| N | 2.40 | 2.33 |

Melting point: 133°–136° C.

| UV-Visible spectrum | |
|---|---|
| 240(1086) | 247(924) |
| 499(362) | 292(228) |
| (in acidic methanol) | 583(346) |
| | (in alkaline methanol) |

IR spectrum: 3400, 1705, 1640, 1620 cm$^{-1}$

Proton NMR spectrum: (in deuterochloroform) $\delta_H$ 0.89(3H, t, J=7.5 Hz, H-14), 1.38(3H, d, J=6.5 Hz, H-6'), 1.6–1.8(4H, m, H-2', H-13), 2.88(1H, dd, J=6.3, 14.5, H-8a), 2.42, 2.59(4H, m, H-3'', 5''), 2.50(1H, m, H-3'), 2.62(1H, J=5.5, 14.5, H-8b), 3.66–3.72(5H, m, H-4', H-2'', 6''), 3.98(1H, q, J=6.5, H-5'), 5.24(1H, dd, J=5.5, 6.3 Hz, H-7), 5.37(1H, brs, H-1'), 7.38(1H, d, J=8.5, 1.0 Hz, H-3), 7.78(1H, dd, J=8.5 Hz, 8.5 Hz, H-2), 7.94(1H, d, J=1.0, 8.5 Hz, H-1).

EXAMPLE 25

In methanol was dissolved 92.8 mg of R20X, and 230.7 mg of josamycin was added. To the mixture was added 23.4 mg of sodium cyanoborohydride, and the mixture was stirred at room temperature for 2 hours, concentrated and subjected to silica gel thin-layer chromatography with a solvent system of chloroform-methanol (10:1). The colored fraction was scraped off, eluted with a mixed solvent of chloroform-methanol, concentrated and subjected to gel filtration on Sephadex LH20 with a system of chloroform-methanol (1:1) to obtain 103.0 mg of N-[18''-(18''-deoxojosamycinyl)]-13-deoxocarminomycin.

Physicochemical properties of N-[18''-(18''-deoxojosamycinyl)]-13-deoxocarminomycin:
Molecular formula: A, B $C_{68}H_{98}O_{23}N_2$
Molecular weight: 1310 (FD-MS)

| Elementary analysis: | Calculated | Found |
|---|---|---|
| C | 62.27 | 61.98 |
| H | 7.53 | 7.45 |
| N | 2.14 | 2.23 |

Melting point: 147°–151° C.

| UV-Visible spectrum | |
|---|---|
| 234(558) | 234(550) |
| 255(256) | 292(74) |

-continued

| UV-Visible spectrum | |
|---|---|
| 294(82) | 553(112) |
| 494(133) | (in alkaline methanol) |
| 527(92) | |
| (in methanol) | |

IR spectrum: 3450, 1740, 1605 cm$^{-1}$ (KBr).

$^{13}$C NMR spectrum: (in deuterochloroform) (A: anthracycline, M: macrolide) δc 7.3(A-14), 14.8(M-19), 16.9(A-6'), 17.6(M-6''), 18.3(A-13), 18.9(M-6'), 20.0(M-16), 21.0(M-21), 22.3(M-11'', 12''), 25.2(M-7''), 25.4(M-10''), 29.9(M-7), 31.1(M-6), 33.6(M-8), 34.8(M-17), 35.1(A-2'), 36.2(A-10), 36.8(A-8), 37.1(M-2), 40.8(M-14), 41.9(M-7', 8'), 43.4(M-9''), 46.4(A-3'), 58.0(M-18), 63.2(M-5''), 66.7(A-4'), 68.6(M-15), 69.1(M-2'), 69.2(M-3'), 69.3(M-3''), 69.6(A-7), 70.4(A-5'), 71.6(M-3), 72.9(M-9), 75.3(M-4'), 76.9(A-9), 71.6(M-4'''), 84.3(M-5), 96.7(M-1''), 100.8(A-1'), 104.1(M-1'), 109.9(A-11a), 110.7(A-5a), 115.9(A-1), 119.3(A-3), 124.4(A-4a), 129.0(M-11), 130.8(M-13), 132.1(M-12), 133.2(A-6a), 133.6(A-10a), 134.8(A-12a), 136.7(M-10), 138.2(A-2), 156.7(A-6), 157.0(A-11), 162.3(A-4), 169.9(M-1), 170.6(M-20), 172.8(M-8''), 185.7(A-5), 190.0(A-12).

We claim:

1. An anthracycline compound useful as an antitumor agent selected from the group consisting of anthracycline compounds represented by the following general formula

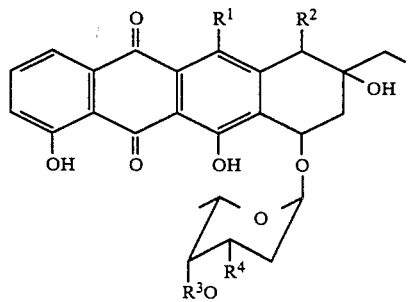

[A]

wherein
(i) R$^1$ is a hydroxyl group
(ii) R$^2$ represents a hydrogen atom or a hydroxyl group
(iii) R$^3$ is a hydrogen atom
(iv) R$^4$ represents one of the following groups (a) to (d)

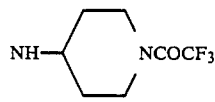 (a)

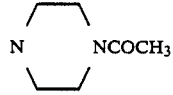 (b)

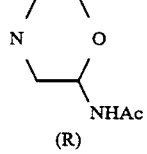 (c)

(R)

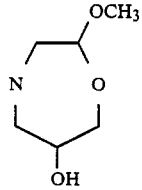 (d)

and if R$^2$ is OH, R$^4$ is not (d).

2. An anthracycline compound according to claim 1 useful as an antitumor agent selected from the group consisting of N-(1''-trifluoroacetyl-4''-piperidinyl)-13-deoxocarminomycin, N-(1'''-trifluoroacetyl-4''-piperidinyl)-13-deoxo-10-hydroxycarminomycin, 3'-deamino-3'-(1''-acetyl-4''-piperazinyl)-13-deoxocarminomycin, 3'-deamino-3'-(1''-acetyl-4''-piperazinyl)-13-deoxo-10-hydroxycarminomycin, 3'-deamino-3'-[(2''R)-2''-acetamido-4''-morpholino]-13-deoxocarminomycin, 3'-deamino-3'-[(2''R)-2''-acetamido-4''-morpholino]-13-deoxo-10-hydroxycarminomycin, and A,B 3'-deamino-3'-(6''-hydroxy-2''-methoxy-4''-perhydroxazepinyl)-13-deoxocarminomycin, wherein A and B are stereoisomers to each other.

* * * * *